(12) United States Patent
Chen et al.

(10) Patent No.: US 12,377,290 B2
(45) Date of Patent: Aug. 5, 2025

(54) PREDICTIVE MAINTENANCE OF DYNAMIC LEAF GUIDE BASED ON DEEP LEARNING

(71) Applicant: Elekta (Shanghai) Technology Co., Ltd., Shanghai (CN)

(72) Inventors: Shufei Chen, Shanghai (CN); Jie Zhou, Shanghai (CN)

(73) Assignee: Elekta (Shanghai) Technology Co., Ltd., Shanghai (CN)

( * ) Notice: Subject to any disclaimer, the term of this patent is extended or adjusted under 35 U.S.C. 154(b) by 512 days.

(21) Appl. No.: 17/596,083

(22) PCT Filed: Nov. 14, 2019

(86) PCT No.: PCT/CN2019/118400
§ 371 (c)(1),
(2) Date: Dec. 2, 2021

(87) PCT Pub. No.: WO2021/092845
PCT Pub. Date: May 20, 2021

(65) Prior Publication Data
US 2022/0296930 A1    Sep. 22, 2022

(51) Int. Cl.
*A61N 5/10* (2006.01)
*G06N 3/08* (2023.01)

(52) U.S. Cl.
CPC ......... *A61N 5/1075* (2013.01); *A61N 5/1045* (2013.01); *G06N 3/08* (2013.01)

(58) Field of Classification Search
CPC ....... A61N 5/1075; A61N 5/1045; G06N 3/08
(Continued)

(56) References Cited

U.S. PATENT DOCUMENTS

| 2012/0076269 A1 | 3/2012 | Roberts |
| 2019/0017592 A1 | 1/2019 | Berger et al. |
| 2019/0175952 A1* | 6/2019 | Hissoiny ............. A61N 5/1049 |

FOREIGN PATENT DOCUMENTS

| CN | 101694182 | 4/2010 |
| CN | 105466670 | 4/2016 |

(Continued)

OTHER PUBLICATIONS

CN 110215581 A English machine translation (Year: 2019).*
(Continued)

*Primary Examiner* — Lee E Rodak
*Assistant Examiner* — Byung Ro Lee
(74) *Attorney, Agent, or Firm* — Schwegman Lundberg & Woessner, P.A.

(57) ABSTRACT

Systems and methods for detecting and diagnosing faults in a radiotherapy system, such as a fault related to a dynamic leaf guide (DLG), are discussed. An exemplary predictive maintenance system includes a processor configured to receive machine data indicative of configuration and operation of a DLG in a target radiotherapy machine, apply a trained deep learning model to the received machine data, and detect and diagnose a DLG fault. The predictive maintenance system can train the deep learning model using data sequences constructed from the received machine data of the one more normal DLGs and the one or more faulty DLGs.

(Continued)

Diagnosis of the DLG fault in the target radiotherapy machine includes classifying the DLG faults into different fault types or different fault severities.

23 Claims, 15 Drawing Sheets

(58) Field of Classification Search
USPC .......................................................... 702/184
See application file for complete search history.

(56) References Cited

FOREIGN PATENT DOCUMENTS

| CN | 107942854 | A | 4/2018 |
|----|-----------|---|--------|
| CN | 109771842 |   | 5/2019 |
| CN | 109800861 | A | 5/2019 |
| CN | 109883699 | A | 6/2019 |
| CN | 110215581 | A | 9/2019 |
| CN | 110261394 |   | 9/2019 |
| CN | 115243759 |   | 9/2024 |
| JP | 2011147592|   | 8/2011 |
| JP | 5289346   | B2| 9/2013 |
| WO | 2019164906|   | 8/2019 |
| WO | WO-2021092845 | A1 | 5/2021 |

OTHER PUBLICATIONS

JP 5289346 B2 English machine translation (Year: 2013).*
CN 109800861 A English machine translation (Year: 2019).*
"European Application Serial No. 19952387.9, Response to Communication pursuant to Rules 161 and 162 filed Oct. 31, 2022", 11 pgs.
"European Application Serial No. 19952387.9, Extended European Search Report mailed Jul. 3, 2023", 6 pgs.
"International Application Serial No. PCT/CN2019/118400, International Search Report mailed Aug. 12, 2020", 4 pgs.
"International Application Serial No. PCT/CN2019/118400, Written Opinion mailed Aug. 12, 2020", 5 pgs.
"European Application Serial No. 19952387.9, Response filed Dec. 15, 2023 to Extended European Search Report mailed Jul. 3, 2023", 18 pgs.
"Chinese Application Serial No. 201980103429.4, Office Action mailed Apr. 22, 2024", W English Translation, 26 pgs.
"Chinese Application Serial No. 201980103429.4, Response filed Jun. 21, 2024 to Office Action mailed Apr. 22, 2024", w current English claims, 16 pgs.

* cited by examiner

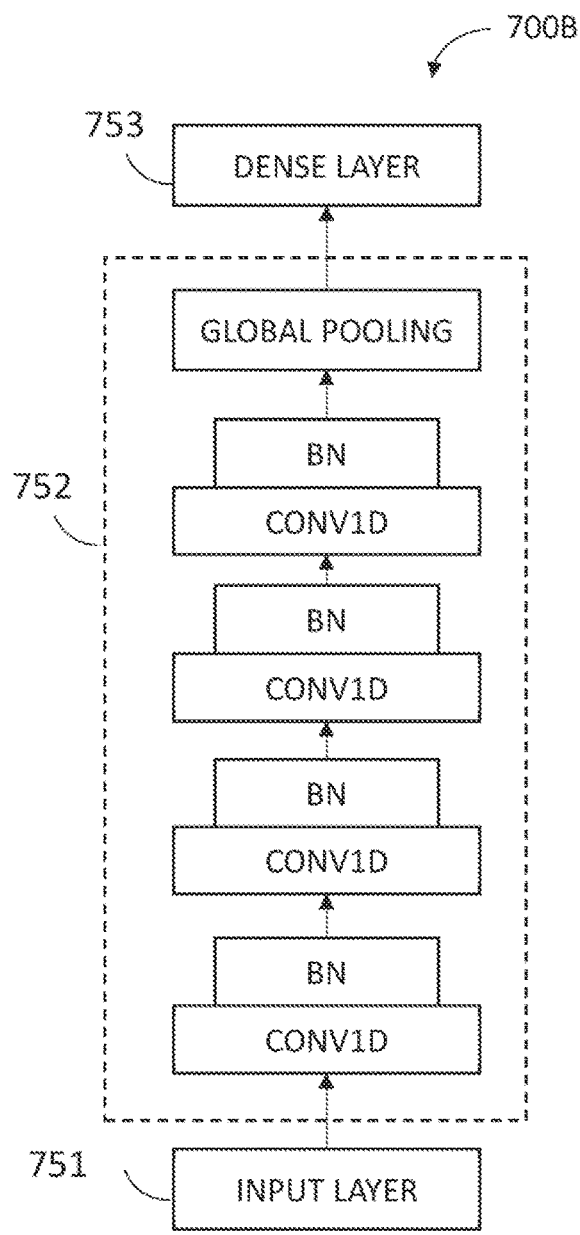
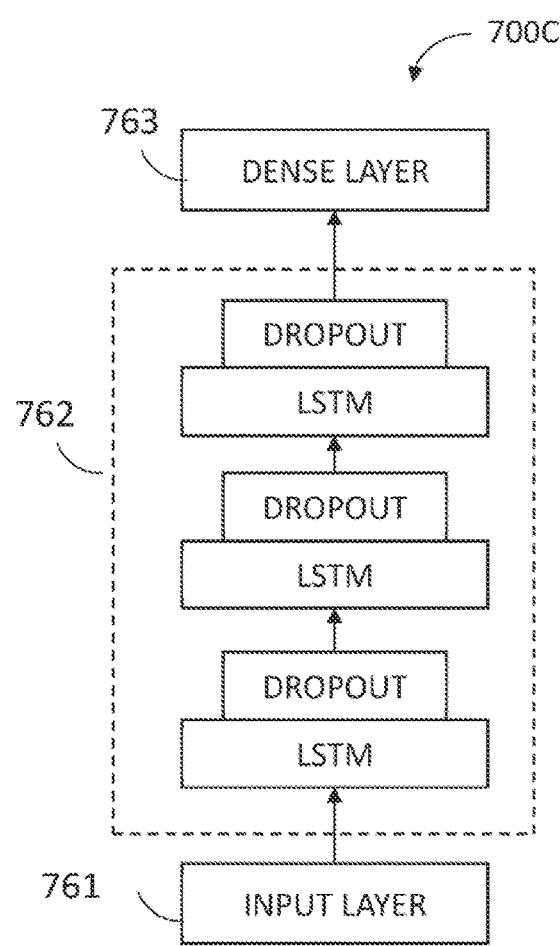
*FIG. 7B*  *FIG. 7C*

PREDICTIVE MAINTENANCE OF DYNAMIC LEAF GUIDE BASED ON DEEP LEARNING

PRIORITY APPLICATIONS

This application is a U.S. National Stage Filing under 35 U.S.C. § 371 from International Application No. PCT/CN2019/118400, filed on Nov. 14, 2019, and published as WO2021/092845 on May 20, 2021; the benefit of priority of which is hereby claimed herein, and which application and publication is hereby incorporated herein by reference in their entirety.

TECHNICAL FIELD

This document relates generally to fault detection and diagnosis (FDD) of a radiation therapy treatment system, and more particularly, to systems and methods of detecting and diagnosing faults associated with a dynamic leaf guide (DLG) in a radiotherapy machine.

BACKGROUND

Radiation therapy (or "radiotherapy") can be used to treat cancers or other ailments in mammalian (e.g., human and animal) tissue. One such radiotherapy technique is provided using a linear accelerator (also referred to as "linac"), whereby a tumor is irradiated by high-energy particles (e.g., electrons, protons, ions, high-energy photons, and the like). The placement and dose of the radiation beam must be accurately controlled to ensure the tumor receives the prescribed radiation, and the placement of the beam should be such as to minimize damage to the surrounding healthy tissue, often called the organ(s) at risk (OARs). A physician prescribes a predefined amount of radiation dose to the tumor and surrounding organs similar to a prescription for medicine. Generally, ionizing radiation in the form of a collimated beam is directed from an external radiation source toward a patient.

A specified or selectable beam energy can be used, such as for delivering a diagnostic energy level range or a therapeutic energy level range. Modulation of a radiation beam can be provided by one or more attenuators or collimators (e.g., a multi-leaf collimator (MLC)). The intensity and shape of the radiation beam can be adjusted by collimation to avoid damaging healthy tissue (e.g., OARs) adjacent to the targeted tissue by conforming the projected beam to a profile of the targeted tissue.

A radiotherapy system, such as a linac system, may include many components. Faults or failure of one or more components may cause operational errors, unexpected malfunction, or even system breakdown. In some cases such component faults or failures may impact the treatment efficacy or patient safety. Preventive inspection and maintenance of the equipment and components may help reduce or eliminate equipment failure and inadvertent interruption and to plan regular activities. Alternatively, predictive maintenance may be used, which includes periodic or continuous monitoring and evaluation of health condition and operational status of in-service equipment to predict a likelihood of a future component fault or failure. Accurate prediction, detection, and diagnosis of component faults or failure can reduce cost associated with maintenance and service of a radiotherapy system.

OVERVIEW

MR-linac is a radiation treatment system that combines linac radiotherapy with diagnostic-level magnetic resonance imaging (MRI). The MR-linac can enable in-room MRI for anatomic and physiological treatment adaptation and response monitoring, and has a potential to reduce treatment margins with real-time visualization and target tracking. Tumors and surrounding tissue can be precisely located, their movement tracked, and treatment adapted in real time in response to changes in tumor position, shape, biology and spatial relationship to critical organs at the time of treatment.

An MR-linac system can include a multileaf collimator (MLC) for shaping, directing, or modulating an intensity of a radiation therapy beam to the specified target locus within the patient. The MLC is made up of collimating elements known as leaves that can move independently in and out of the path of a radiotherapy beam to shape it and vary its intensity. Conformal radiotherapy and Intensity Modulated Radiation Therapy (IMRT) can be delivered using MLCs. For example, in conformal radiotherapy, the MLC allows conformal shaping of the beam to match the borders of the target tumor. For intensity modulated treatments, the leaves of a MLC can be moved across the field to create IMRT distributions.

Collimating elements of an MLC can move at a high speed during operation. For example, Agility™ MLC (Elekta AB, Sweden) has 160 interdigitating leaves with 5 mm width at isocenter. The leaves are arranged in two banks of 80 leaves, where each bank of leaves are contained within a dynamic leaf guide (DLG) that moves with the MLC leaves. The MLC leaves and the DLG can be digitally controlled to provide accurate leaf positioning. The maximum velocity of individual MLC leaves can be up to 35 mm per second (mm/s), and the DLG can move at a speed up to 30 mm/s. As such, when both the DLG and the MLC move in the same direction, the MLC leaves can move at a speed up to 65 mm/s.

The MLC leaves and DLG may be subject to fault or failure during ordinary use of a radiotherapy machine. For example, a faulty or failed DLG may be associated with malfunctions of one or more sub-components, such as a brake, a circuit board, a drive motor, a linear slide, or a coupling of the DLG. Proper and timely prediction or detection of a DLG fault, and accurate diagnosis of root cause of said fault (e.g., classifying a detected fault as one or more fault types such as a 10 brake fault, a circuit board fault, or a drive motor fault) can be an important part of predictive maintenance of a radiotherapy system.

Conventional predictive maintenance approaches face some challenges in the context of machine fault detection and diagnosis (FDD) of a radiation therapy treatment system, such as FDD of a DLG or MLC in a linac system. For example, many conventional predictive maintenance are based on a complex physical model. Such a model typically involves complicated mathematical formulae and a large number of parameters of machine characteristics (e.g., friction coefficient, vibration speed, pressure, temperature, current and voltage attributes). The FDD process includes fitting the machine or component data to the physical model. However, to build a complex physical model generally requires substantial domain knowledge and skills and expertise (e.g. in physics, medicine, and engineering) of a human designer. This can be time consuming, and can increase design complexity and overall development cost. For example, feature extraction and feature engineering (e.g., feature selection, feature dimension reduction, and feature optimization) as required to build a physical model can be time-consuming and resource-intensive tasks. Additionally, a physical model is generally constructed based on some assumptions about what is considered normal or abnormal operating characteristics of a component in a radiotherapy system. However, the operating characteristics of a component can be different from one model to another model, or from one manufacturer to another manufacturer. As such, the physical models developed under these assumptions may be less adaptable to different machine or systems. The FDD performance can be compromised when some assumptions do not hold. The present inventors have recognized an unmet need for advanced techniques such as self-learning of various types of machine faults to improve predictive maintenance of a radiotherapy system.

The present document describes a predictive maintenance model based on deep learning, and use such a model to detect and diagnose faults associated with a part of a linac system, such as a DLG. An exemplary predictive maintenance system includes a processor configured to receive machine data indicative of configuration and operation of a DLG in a target radiotherapy machine, apply a trained deep learning model to the received machine data, and 10 detect and diagnose a DLG fault. The predictive maintenance system can train the deep learning model using a plurality of data sequences generated from the received machine data of the one more normal DLGs and the one or more faulty DLGs. Diagnosis of the DLG fault in the target radiotherapy machine includes a classification of DLG fault into one or more fault types associated with various components of the DLG driving system.

In this document, terms such as "fault detection", "fault diagnosis", and "fault detection and diagnosis (FDD)" are used throughout. "Fault detection" includes detecting a matured fault, and/or an impending fault. A matured fault can be one that has caused detectable malfunctions or faulty operation of at least a portion of the radiotherapy system. An impending fault can be a fault that is anticipated to occur (such as according to a prediction algorithm) in a near future from the time of a prediction is made. As such, "fault detection" as used in this document can refer to detecting a mature fault, and/or predicting an impending fault. "Fault diagnosis" may refer to a process of recognizing a root cause of the fault, classifying a detected fault (a mature fault or an impending fault) into one of a plurality of fault types, classifying a detected fault into one of a plurality of fault severity levels such as based on a DLG metric trend, and/or generating fault analytics.

Example 1 is a computer-implemented method for detecting and diagnosing a fault in a radiotherapy machine. The method comprises steps of: receiving machine data indicative of configuration and operation of a component in a target radiotherapy machine; applying a trained deep learning model to the received machine data of the component in the target radiotherapy machine, the trained deep learning model being trained to establish a relationship between (1) machine data collected from normal components and faulty components in respective radiotherapy machines, and (2) fault information of the normal components and the faulty components, the normal components and the faulty components being of the same type as the component in the target radiotherapy machine; and detecting and diagnosing a fault associated with the component in the target radiotherapy machine.

In Example 2, the subject matter of Example 1 optionally includes steps of: receiving the machine data collected from the normal components and the 10 faulty components with respectively identified faults, the machine data indicative of configuration and operation of respective components; constructing a training dataset including a plurality of data sequences generated from the received machine data of the normal components and the faulty components; and training a deep learning model using the constructed training dataset to establish the trained deep learning model.

In Example 3, the subject matter of Example 2 optionally includes the component in the target radiotherapy machine that can include a dynamic leaf guide (DLG), the normal components that can include normal DLGs, and the faulty components that can include faulty DLGs with respectively identified DLG faults. The step of detecting and diagnosing the fault can include detecting and diagnosing a DLG fault in the target radiotherapy machine.

In Example 4, the subject matter of Example 3 optionally includes training the deep learning model that can include: applying respective penalty weights to one or more of the plurality of data sequences in the training dataset; and training the deep learning model using the constructed training dataset including the weighted data sequences.

In Example 5, the subject matter of any one or more of Examples 3-4 optionally includes the deep learning model being trained that can include one or more of: a convolutional neural network (CNN); a recurrent neural network (RNN); a long-term and short-term memory (LSTM) network; a deep belief network (DBN); or a transfer learning module.

In Example 6, the subject matter of any one or more of Examples 3-5 optionally include generating the plurality of data sequences including a trend of DLG current measurements over time, the DLG current measured respectively from one or more DLGs at respective axes.

In Example 7, the subject matter of Example 6 optionally includes the DLG current trend that can include one or more of: a trend of daily average current; a trend of daily variation current; a trend of daily maximum current; a trend of multiday moving-average of current.

In Example 8, the subject matter of any one or more of Examples 3-7 optionally includes generating the plurality of data sequences including a trend of a DLG position metric over time, the DLG position metric calculated respectively 10 for one or more DLGs at respective axes.

In Example 9, the subject matter of Example 8 optionally includes the DLG position metric that can include a count of DLG out-of-position events occurred during a specific time period, and the DLG position trend that can include one or more of: a trend of daily count of out-of-position events; or a trend of cumulative count of out-of-position events over a specified number of days.

In Example 10, the subject matter of any one or more of Examples 3-9 optionally include generating the plurality of data sequences that can include a trend of alarms triggered by one or more alarm events, the alarm trends that can include one or more of: a trend of daily count of alarms; or a trend of cumulative count of alarms over a specified number of days.

In Example 11, the subject matter of any one or more of Examples 3-10 optionally includes constructing the training dataset that can include assigning a fault type to each of the plurality of data sequences, and wherein diagnosing the DLG fault in the target radiotherapy machine includes classifying a DLG fault as one or more fault types including: a DLG brake fault; a DLG drive circuit board fault; a DLG drive motor fault; a DLG slide fault; or a DLG coupling unit fault.

In Example 12, the subject matter of any one or more of Examples 3-11 optionally includes constructing the training dataset that can include assigning a respective fault severity level to each of the plurality of data sequences, and wherein diagnosing the DLG fault in the target radiotherapy machine includes classifying a DLG fault as one of a plurality of fault severity levels.

In Example 13, the subject matter of any one or more of Examples 3-12 optionally includes training the deep learning model that can include determining for each of the plurality of data sequences a corresponding remaining useful life (RUL), and establishing a relationship between the plurality of data sequences and the corresponding determined RULs. The method can further include using the trained deep learning model to predict a RUL for the DLG in the target radiotherapy machine.

In Example 14, the subject matter of any one or more of Examples 3-13 optionally includes training the deep learning model that can include adjusting one or more model parameters to minimize a cost function, the cost function including a penalty term based on a Matthews Correlation Coefficient (MCC). 10 [0026] Example 15 is a system for detecting and diagnosing a fault in a radiotherapy machine configured to provide radiation therapy to a subject. The system comprises a processor configured to: receive machine data indicative of configuration and operation of a component in a target radiotherapy machine; apply a trained deep learning model to the received machine data of the component in the target radiotherapy machine, the trained deep learning model being trained to establish a relationship between (1) machine data collected from normal components and faulty components in respective radiotherapy machines, and (2) fault information of the normal components and the faulty components, the normal components and the faulty components being of the same type as the component in the target radiotherapy machine; and detect and diagnose a fault associated with the component in the target radiotherapy machine.

In Example 16, the subject matter of Example 15 optionally includes the processor that can include a training module configured to: receive the machine data collected from the normal components and the faulty components with respectively identified faults, the machine data indicative of configuration and operation of respective components; construct a training dataset including a plurality of data sequences generated from the received machine data of the normal components and the faulty components; and establish the trained deep learning model by training a deep learning model using the constructed training dataset.

In Example 17, the subject matter of Example 16 optionally includes the component in the target radiotherapy machine that can include a dynamic leaf guide (DLG), the normal components that can include normal DLGs, and the faulty components that can include faulty DLGs with respectively identified DLG faults. The processor can be configured to detect and diagnose a DLG fault in the target radiotherapy machine.

In Example 18, the subject matter of Example 17 optionally includes the processor that can be configured to construct the training dataset using fault information of each of the plurality of data sequences, the fault information including an indicator of fault presence or absence, fault type, or fault severity level.

In Example 19, the subject matter of any one or more of Examples 17-10 18 optionally includes the training module that can be configured to generate the plurality of data sequences including one or more of: a trend of DLG current measurements over time; a trend of a DLG position metric over time, the DLG position metric including a count of DLG out-of-position events occurred during a specific time period; or a trend of a count of alarms triggered by one or more alarm events.

Example 20 is a non-transitory machine-readable storage medium that includes instructions that, when executed by one or more processors of a machine, cause the machine to perform operations comprising receiving machine data indicative of configuration and operation of a component in a target radiotherapy machine; applying a trained deep learning model to the received machine data of the component in the target radiotherapy machine, the trained deep learning model being trained to establish a relationship between (1) machine data collected from normal components and faulty components in respective radiotherapy machines, and (2) fault information of the normal components and the faulty components, the normal components and the faulty components being of the same type as the component in the target radiotherapy machine; and detecting and diagnosing a fault associated with the component in the target radiotherapy machine.

In Example 21, the subject matter of Example 20 optionally includes the operations that further comprise: receiving the machine data collected from the normal components and the faulty components with identified faults, the machine data indicative of configuration and operation of respective components; constructing a training dataset including a plurality of data sequences generated from the received machine data of the normal components and the faulty components; and training a deep learning model using the constructed training dataset to establish the trained deep learning model.

In Example 22, the subject matter of Example 21 optionally includes the component in the target radiotherapy machine that can include a dynamic leaf guide (DLG), the normal components that can include normal DLGs, and the faulty components that can include faulty DLGs with respectively identified DLG faults. The option of detecting and diagnosing the fault can include detecting and diagnosing a DLG fault in the target radiotherapy machine.

In Example 23, the subject matter of Example 22 optionally include the 10 operations that further comprise diagnosing the DLG fault in the target radiotherapy machine includes classifying a DLG fault as one or more of: a DLG brake fault; a DLG drive circuit board fault; a DLG drive motor fault; a DLG slide fault; or a DLG coupling unit fault.

The predictive maintenance based on deep learning as discussed in the present document improves FDD accuracy and maintenance efficiency. Compared to conventional FDD based on physical models, the deep learning model discussed herein advantageously learns characteristics of different fault types from a sequence of measurements from a component in radiotherapy system, such as a DLG in a linac system. The deep-learning based predictive maintenance systems, apparatus, and methods as discussed in this document may also be applied to maintenance of related issues for Gun, Vacuum, Magnetron and other critical linac parts and features. The present document further discusses various techniques to boost the performance of deep learning, including training data balancing based on penalty weight, fusion of different deep learning models, and transfer learning. The resultant model can efficiently learn independently different fault features. The number of features learned by the deep learning model discussed herein can be substantially higher than what an artificially designed feature extractor of a conventional FDD model can offer. Additionally, the deep learning model discussed herein may be adapted to different radiotherapy machines with a higher generality than the conventional FDD models that are platform dependent.

Conventional FDD models generally have a pipelined architecture, where multiple intermediate modules (e.g., feature extraction and fault classification) are to be designed, trained, and optimized separately. Such modularized training and optimization require substantial domain knowledge and longer development time and higher development cost. In contrast, the deep learning model discussed herein provides an "end-to-end" (E2E) solution to FDD. According to various embodiments, a convoluted neural network (or other types of neural networks) can take as input a sequence of measurements (e.g., a time series) a DLG parameter, and directly produce fault detection and diagnosis as output. In contrast to the pipeline architecture, all the parameters and network structures can be trained simultaneously. With improved accuracy and higher efficiency of fault prediction and diagnosis, the number of unnecessary machine servicing, testing, 10 and possible shutdowns, along with the associated maintenance cost, can be substantially reduced. Costly machine breakdowns can be reduced or even eliminated in some cases due to the ability to detect faults earlier before they can do much damage.

The above is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

FIG. 7B is a block diagram illustrating an exemplary convoluted neural network (CNN) that may be constructed and trained according to the process shown in FIG. 7A.

FIG. 7C is a block diagram illustrating an exemplary recurrent neural network (RNN), specifically a long short-term memory (LSTM) network, that may be constructed and trained according to the process shown in FIG. 7A.

DETAILED DESCRIPTION

In the following detailed description, reference is made to the accompanying drawings which form a part hereof, and which is shown by way of illustration-specific embodiments in which the present disclosure may be practiced. These embodiments, which are also referred to herein as "examples," are described in sufficient detail to enable those skilled in the art to practice the disclosure, and it is to be understood that the embodiments may be combined, or that other embodiments may be utilized and that structural, logical and electrical changes may be made without departing from the scope of the present disclosure. The following detailed description is, therefore, not be taken in a limiting sense, and the scope of the present disclosure is defined by the appended aspects and their equivalents.

Figure 1:
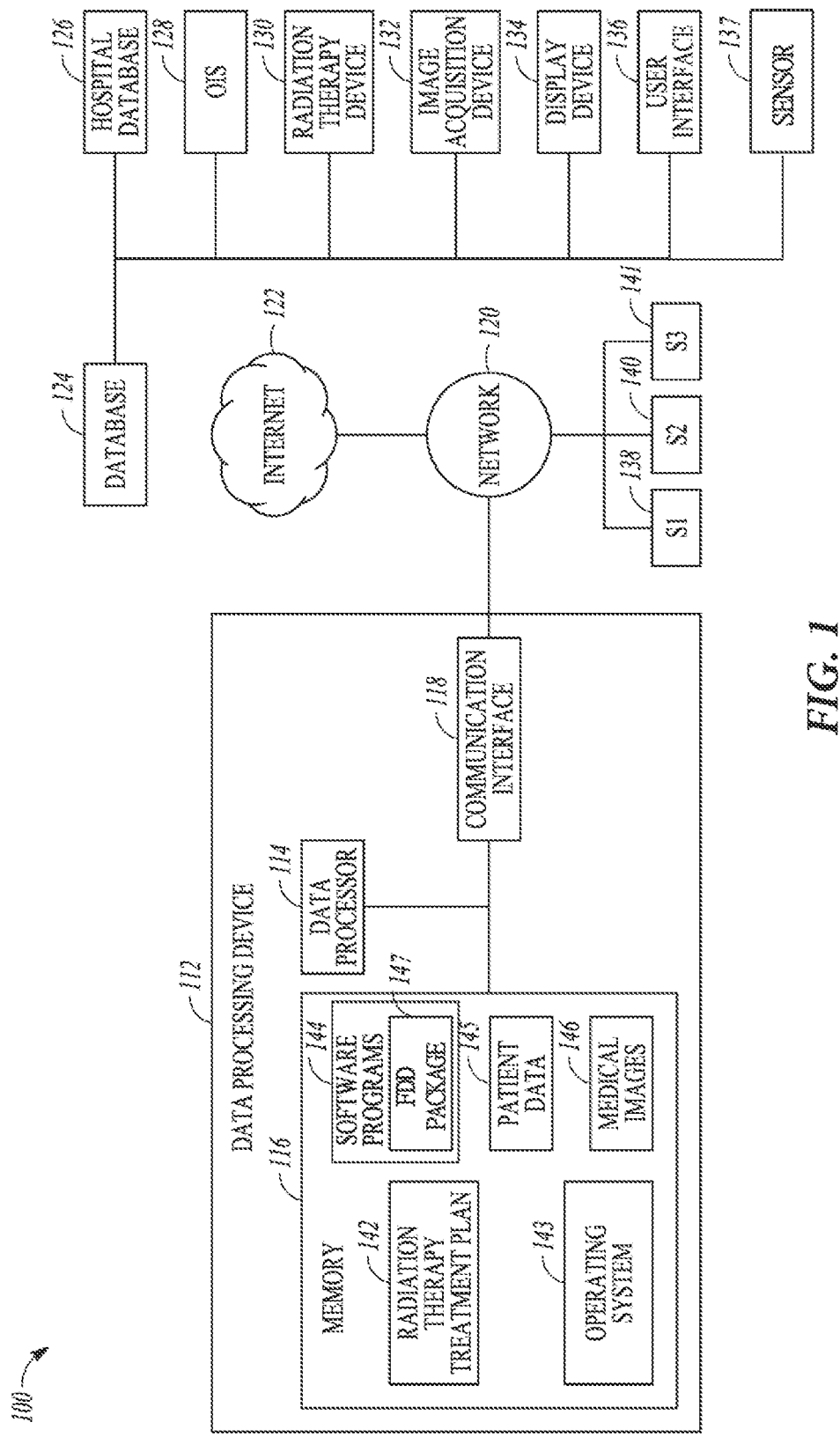
FIG. 1 illustrates an exemplary radiotherapy system.

FIG. 1 illustrates an exemplary radiotherapy system 100 for providing radiation therapy to a patient, The radiotherapy system 100 includes an data processing device 112. The data processing device 112 may he connected to a network 120. The network 120 may be connected to the Internet 122. The network 10 120 can connect the data processing device 112 with one or more of a database 124, a hospital database 126, an oncology information system (OIS) 128, a. radiation therapy device 130, an image acquisition device 132, a display device 134, and a user interface 136. The data processing device 112 can be configured to generate radiation therapy treatment plans 142 to be used by the radiation therapy device 130.

The data processing device 1.12 may include a memory device 116, a processor 114, and a communication interface 118. The memory device 116 may store computer-executable instructions, such as an operating system 143. a radiation therapy treatment plan 142 (e.g., original treatment plans, adapted treatment plans and the like), software programs 144, and any other computer-executable instructions to be executed by the processor 114. The memory device 116 may additionally store data, including medical images 146, patient data 145, and other data required to implement a radiation therapy treatment plan 142.

The software programs 144 may include radiotherapy treatment plan software implementing algorithms of artificial intelligence, deep learning, and neural networks, among others. in an example, the software programs 144 can convert medical images of one format (e.g., MRI) to another format (e.g., CT) by producing synthetic images, such as pseudo-CT images. For instance, the software programs 144 may include image processing programs to train a predictive model for converting a medical image from the medical images 146 in one modality (e.g., an MRI image) into a synthetic image of a different modality (e.g., a pseudo CT image); alternatively, the trained predictive model may convert a CT image into an MRI image. In another example, the software programs 144 may register the patient image (e.g., a CT image or an MR image) with that patient's dose distribution (also represented as an image) so that corresponding image voxels and dose yawls are associated appropriately by the network. In yet another example, the software programs 144 may substitute functions of the patient images such as signed distance functions or processed versions of the images that emphasize some aspect of the image information. Such functions might emphasize edges or differences in voxel textures, or any other structural aspect useful to neural network learning. The software programs 144 may substitute functions of the dose distribution that emphasize some aspect of the dose information. Such functions 10 might emphasize steep gradients around the target or any other structural aspect useful to neural network learning.

In an example, the software programs 144 may generate projection images for a set of two-dimensional (2D) and/or 3D CT or MR images depicting an anatomy (e.g., one or more targets and one or more OARs) representing different views of the anatomy from a first gantry angle of the radiotherapy equipment. For example, the software programs 144 may process the set of CT or MR images and create a stack of projection images depicting different views of the anatomy depicted in the CT or MR images from various perspectives of the gantry of the radiotherapy equipment. In particular, one projection image may represent a view of the anatomy from 0 degrees of the gantry, a second projection image may represent a view of the anatomy from 45 degrees of the gantry, and a third projection image may represent a view of the anatomy from 90 degrees of the gantry. The degrees may be a position of the MLC relative to a particular axis of the anatomy depicted in the CT or MR images. The axis may remain the same for each of the different degrees that are measured.

in an example, the software programs 144 may generate graphical aperture image representations of MLC leaf positions at various gantry angles. These graphical aperture images are also referred to as aperture images. In particular, the software programs 144 may receive a set of control points that are used to control a radiotherapy device to produce a radiotherapy beam. The control points may represent the beam intensity, gantry angle relative to the patient position, and the leaf positions of the MLC, among other machine parameters. Based on these control points, a graphical image may be generated to graphically represent the beam shape and intensity that is output by the MLC at each particular gantry angle. The software programs 144 may align each graphical image of the aperture at a particular gantry angle with the corresponding projection image at that angle that was generated. The images are aligned and scaled with the projections such that each projection image pixel is aligned with the corresponding aperture image pixel.

In an example, the software programs 144 store a treatment planning software. The treatment planning software may include a trained machine learning model to generate or estimate a graphical aperture image representation of MLC 10 leaf positions at a given gantry angle for a projection image of the anatomy representing the view of the anatomy from the given gantry angle. The software programs 144 may further include a beam mod& to compute machine parameters or control points for a given type of machine to output a beam from the MLC that achieves the same or similar estimated graphical aperture image representation of the MLC leaf positions. Namely, the treatment planning software may output an image representing an estimated image of the beam shape and intensity for a given gantry angle and for a given projection image of the gantry at that angle, and the function may, compute the control points for a given radiotherapy device to achieve that beam shape and intensity.

In some examples, the software programs 144 may include a machine fault detection and diagnosis (EDD) software package 147. The EDD software package 147 can include a trained deep learning model, such as a convolutional neural network (CNN), a recurrent neural network. (RNN), a deep belief network (DBN), or a hybrid neural network comprising two or more neural network models of different types or different model configurations A predictive maintenance system, which can be a sub-system of the radiotherapy system 100, can be configured to perform predictive machine maintenance using the FDD software package 147. In an example, the trained deep learning model can be used to detect and diagnose a fault of a part of a radiotherapy machine, such as a DLG in a linac system. Examples of training the deep learning model and using said model to detect and diagnose faults associated with a DLG are discussed below, such as with reference to FIGS. 7-9.

In addition to the memory 116 storing the software programs 144, the software programs 144 may additionally or alternatively be stored on a removable computer medium, such as a hard drive, a computer disk, a CD-ROM, a DVI), a HD, a Blu-Ray DVD, USB flash drive, a SD card, a memory stick, or any other suitable medium; and the software programs 144 when downloaded to data processing device 112 may be executed by data processor 114.

The data processor 114 may be communicatively coupled to the memory 116, and the processor 114 may be configured to execute computer executable instructions stored therein. The processor 114 may send or receive medical images 146 to the memory 116. For example, the processor 114 may receive medical images 146 from the image acquisition device 132 via the communication interface 118 and network 120 to be stored in memory 116. The processor 114 may also send medical images 146 stored in memory 116 via the communication interface 118 to the network 120 be stored in the database 124 or the hospital database 126.

The data processor 114 may utilize the software programs 144 (e.g., a treatment planning software), along with the medical images 146 and patient data 145, to create the radiation therapy treatment plan 142. Medical images 146 may include information such as imaging data associated with a patient anatomical region, organ, or volume of interest segmentation data. Patient data 145 may include information such as (1) functional organ modeling data (e.g., serial versus parallel organs, appropriate dose response models, etc.); (2) radiation dosage data (e.g., DVH information); or (3) other clinical information about the patient and treatment (e.g., other surgeries, chemotherapy, previous radiotherapy, etc.).

In some examples, the data processor 114 (or a separate processor) can be a part of a predictive maintenance system configured to perform predictive machine maintenance such as detecting and diagnosing machine faults or failure. The data processor 114 may execute the FDD software package 147 to generate detection and diagnosis of a fault, such as a fault associated with a DLG of a target radiotherapy machine. Machine data indicative of configuration and operational status of the DLG (also referred to as DLG data), can be sensed using one or more sensors 137, or sensors or measurement devices separate from the radiotherapy system 100. The DLG data can be stored in the database 124. In some examples, at least some DLG data may be provided to the radiotherapy system 100 via an input device such as in a user interface 136, and stored in the database 124. The data processor 114 can receive the DLG data stored in the database 124, and execute the FDD software package 147 to detect a DLG fault, diagnose the DLG fault as being attributed to one or more of a brake fault, circuit board fault, or drive motor fault, determining a severity of the DLG fault, or to predict a time to fault (or the remaining useful life, or "RUL").

In some examples, the data processor 114, being a part of a predictive maintenance system, can be configured to train a deep learning model using data collected from one or more normal (fault-free) DLGs of respective linac machines and data collected from one or more faulty DLGs of respective linac machines with known or expert-adjudicated fault types. The DLG data, along with the corresponding fault labels representing fault presence/absence or fault type, are collectively referred to as the training data, and can be provided to the data processor 114 to train a deep learning model. The trained deep learning model, when meeting a specified training convergence criterion, can be stored in the memory 116 or the database 124.

In addition, the processor 114 may utilize software programs to generate intermediate data such as updated parameters to be used, for example, by a machine learning model, such as a. neural network model; or generate intermediate 2D or 3D images, which may then subsequently be stored in memory 116. The processor 114 may subsequently then transmit the executable radiation therapy treatment plan 142 via the communication interface 118 to the network 120 to the radiation therapy device 130, where the radiation therapy plan can be used to treat a patient with radiation. In addition, the processor 114 may execute software programs 144 to implement functions such as image conversion, image segmentation, deep learning, neural networks, and artificial intelligence, For instance, the processor 114 may execute software programs 144 that train or contour a. medical image; such software; programs144 when executed may train a. boundary detector or utilize a shape dictionary.

The processor 114 may be a processing device, include one or more general-purpose processing devices such as a microprocessor, a central processing unit (CPU), a graphics processing unit (GPU), an accelerated processing unit (APU), or the like. More particularly, the processor 114 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 114 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments. the processor 114 may he a special-purpose processor, rather than a general-purpose processor. The processor 114 may include one or more known processing devices, such as a microprocessor from the Pentitium™, Core™, Xeon™, or Itanium™, family manufactured by Intel™, the Turion™, Athlon™, Sempron™, Opteron™, FX™, Phenom™ family manufactured by AMD™, or any of various processors manufactured by Sun Microsystems. The processor 114 may also include graphical processing units such as a GPU from the GeForce®, Quadro®, Tesla® family manufactured by NVidia™, GMA, Iris™ family manufadured by Intel™, or the Radeonm™ family manufadured by AMD™. The processor 114 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor (for example, a multi-core design or a plurality of processors each having a multi-core design). The processor 114 can execute sequences of computer program instructions, stored in memory 116, to perform various operations, processes, methods as to be explained in greater detail below.

The memory device 116 can store medical images 146. In some embodiments, the medical images 146 may include one or more MRI images (e.g., 2D MRI, 3D MRI, 2D streaming MRI, four-dimensional (4D) MRI, 4D volumetric MRI, 4D cine MRI, etc.), functional MRI images (e.g., fMRI, DCE-MRI, diffusion MRI). CT images (e.g., 2D CT, cone beam CT. 3D CT, 4D CT), ultrasound images (e.g., 2D ultrasound, 3D ultrasound, 4D ultrasound), one or more projection images representing views of an anatomy depicted in the MRI, synthetic CT (pseudo-CT), and/or CT images at different angles of a gantry relative to a patient axis, PET images, X-ray images, fluoroscopic images, radiotherapy portal images, SPECT images, computer generated synthetic images (e.g., pseudo-CT images), aperture images, graphical aperture image representations of MLC leaf positions at different gantry angles, and the like. Further, the medical images 146 may also include medical image data, for instance, training images, and ground truth images, contoured images, and dose images. In an embodiment, the medical images 146 may be received from the image acquisition device 132. Accordingly, image acquisition device 132 may include an MRI imaging device, a CT imaging device, a PET imaging device, an ultrasound imaging device, a fluoroscopic device, a SPECT imaging device, an integrated linac and MRI imaging device, or other medical imaging devices for obtaining the medical images of the patient. The medical images 146 may be received and stored in any type of data or any type of format that the data processing device 112 may use to perform operations consistent with the disclosed embodiments.

The memory device 116 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a CD-ROM, as DVD Of other optical storage, a cassette tape other magnetic storage device, or any other non-transitory medium that may be used to store information including image, data, or computer executable instructions (e.g., stored in any format) capable of being accessed by the processor 114, or any other type of computer device. The computer program instructions can he accessed by the processor 114, read from the ROM, or any other suitable memory location, and loaded into the RAM for execution by the processor 114. For example, the memory 116 may store one or more software applications. Software applications stored in the memory 116 may include, for example, an operating system 143 for common computer systems as well as for software-controlled devices. Further, the memory 116 may store an entire software application, or only a part of a software application, that are executable by the processor 114. For example, the memory device 116 may store one or more radiation therapy treatment plans 1.42, The data processing device 112 can communicate with the network 120 via the communication interface 118, which can be communicatively coupled to the processor 114 and the memory 116. The communication interface 118 may provide communication connections between the data processing device 112 and radiotherapy system 100 components (e.g., permitting the exchange of data with external devices). For instance, the communication interface 118 may in some embodiments have appropriate interfacing circuitry to connect to the user interface 136, which may be a hardware keyboard, a keypad, or a touch screen through which a user may input information into radiotherapy system 100.

Communication interface 118 may include, for example, a network adaptor, a cable connector, a serial connector, a USB connector, a parallel connector, a high-speed data transmission adaptor (e.g., such as fiber, USB 3,0, thunderbolt, and the like), a wireless network adaptor (e.g., such as a WiFi adaptor), a telecommunication adaptor (e.g., 3G, 4G/LTE and the like), and the like. Communication interface 118 may include one Of more digital and/or analog communication devices that permit data processing device 112 to communicate with other machines and devices, such as remotely located components, via the network 120.

The network 120 may provide the functionality of a local area network (LAN), a wireless network, a. cloud computing environment (e.g., software as a. service, platform as a service, infrastructure as a service, etc,), a client-server, a wide area network (WAN), and the like. For example, network 120 may be a LAN or a WAN that may include other systems S1 (138), S2 (140), and S3 (141). Systems S1, S2, and S3 may be identical to data processing device 112 or may be different systems. In some embodiments, one or more of systems in network 120 may form a distributed computing/simulation environment that collaboratively performs the embodiments described herein, in some embodiments, one or more systems S1, S2, and S3 may include a CT scanner that obtains CT images (e.g., medical images 146). In addition, network 120 may be connected to Internet 122 to communicate with servers and clients that reside remotely on the internet.

Therefore, network 120 can allow data transmission between the data processing device 112 and a number of various other systems and devices, such as the OIS 128, the radiation therapy device 130, and the image acquisition device 132. Further, data generated by the MS 128 and/or the image acquisition device 132 may be stored in the memory 116, the database 124, and/or the hospital database 126. The data may be transmitted/received via network 120, through communication interface 118 in order to be accessed by the processor 114, as required.

The data processing device 112 may communicate with database 124 through network 120 to send/receive a plurality of various types of data stored on database 124. For example, the database 124 may store machine data associated with a radiation therapy device 130, image acquisition device 132, or other machines relevant to radiotherapy. The machine data information may include control points, such as radiation beam size, arc placement, beam on and off time duration, machine parameters, segments, MLC configuration, gantry speed, MRI pulse sequence, and the like. In some examples, the database 124 may store machine data representing configuration and operational status of a part of the radiotherapy system 300, such as a DLG of a linac machine. Additionally, the database 124 may store training data that may be used to train a deep learning model for detecting and diagnosing component fault or failure. The training data may include machine data acquired from normal DLGs and faulty DLGs from radiotherapy machines. The database 124 may he a storage device and may be equipped with appropriate database administration software programs. One skilled in the art would appreciate that database 124 may include a plurality of devices located either in a central or a distributed manner.

In some embodiments, the database 124 may include a processor-readable storage medium (not shown). While the processor-readable storage medium in an embodiment may be a single medium, the term "processor-readable storage medium" should be taken to include a single medium or multiple media (e.g., a centralized or distributed database, and/or associated caches and servers) that store the one or more sets of computer executable instructions or data. The term "processor-readable storage medium" shad also be taken to include any medium that is capable of storing or encoding a set of instructions for execution a processor and that cause the processor to perform any one or more of the methodologies of the present disclosure. The term "processor readable storage medium" shad accordingly be taken to include, but not be limited to, solid-state memories, optical and magnetic media. For example, the processor readable storage medium can be one or more volatile, non-transitory, or non-volatile tangible computer-readable media.

The data processor 114 may communicate with the database 124 to 10 read images into memory 116 or store images from the memory 116 to the database 124. For example, the database 124 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DICOM data, projection images, graphical aperture images, etc.) that the database 124 received from image acquisition device 132. Database 124 may store data to he used by the data. processor 114 when executing software program 144, or when creating radiation therapy treatment plans 142. Database 124 may store the data produced by the trained machine leaning mode, such as a neural network including the network parameters constituting the model learned by the network and the resulting predicted data. The data processing device 112 may receive the imaging data, such as a medical image 146 (e.g., 2D MRI slice images, CT images, 2D Fluoroscopy images, X-ray images, 3DMRI images, 4D MRI images, projection images, graphical aperture images, etc.) either from the database 124, the radiation therapy device 130 (e.g., an MR-linac), and or the image acquisition device 132 to generate a treatment plan 142.

In an embodiment, the radiotherapy system 100 can include an image acquisition device 132 that can acquire medical images (e.g., MRI images, 3D MRI., 2D streaming MRL 4D volumetric MRI, CT images, cone-Beam CT, PET images, functional MRI images (e.g., fMRI, DCE-MRI and diffusion MRI), X-ray images, fluoroscopic image, ultrasound images, radiotherapy portal images, SPECT images, and the like) of the patient. Image acquisition device 132 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the image acquisition device 132 can be stored within database 124 as either imaging data and/or test data. By way of example, the images acquired by the image acquisition device 1.32 can be also stored by the data. processing device 112, as medical image 146 in memory 116.

In an embodiment, for example, the image acquisition device 132 may be integrated with the radiation therapy device 130 as a single apparatus. For example, a MR imaging device can he combined with a linear accelerator to form 10 a system referred to as an "MR-linac." Such an MR-linac can be used, for example, to determine a location of a target organ or a target tumor in the patient, so as to direct radiation therapy accurately according to the radiation therapy treatment plan 142 to a predetermined target.

The image acquisition device 132 can he configured to acquire one or more images of the patient's anatomy for a region of interest (e.g., a target organ, a target tumor, <r both). Each image, typically a 2D image or slice, can include one or more parameters (e.g., a 2D slice thickness, an orientation, and a location, etc.). In an embodiment, the image acquisition device 132 can acquire a 2D slice in any orientation. For example, an orientation of the 2D slice can include a sagittal orientation, a. coronal orientation, or an axial orientation. The processor 114 can adjust one or more parameters, such as the thickness and/or orientation of the 2D slice, to include the target organ and/or target tumor. In an embodiment, 2D slices can be determined from information such as a 3D MRI volume. Such 2D slices can be acquired by the image acquisition device 132 in "real-time" while a patient is undergoing radiation therapy treatment, for example, when using the radiation therapy device 130, with "real-time" meaning acquiring the data in at least milliseconds or less.

The data processing device 112 may generate and store radiation therapy treatment plans 142 for one or more patients. The radiation therapy treatment plans 142 may provide information about a particular radiation dose to be applied to each patient. The radiation therapy treatment plans 142 may also include other radiotherapy information, such as control points including beam angles, gantry angles, beam intensity, dose-histogram-volume information, number of radiation beams to be used during therapy, dose per beam, and the like.

The data processor 114 may generate the radiation therapy treatment plan 142 by using software programs 144 such as treatment planning software Monaco®, manufactured. by Elekta AB of Sweden), in order to generate the radiation therapy treatment plans 142, the data processor 114 may communicate with the image acquisition device 132 (e.g., a CT device, an MRI device, a PET device, an X-ray device, an ultrasound device, etc.) to access images of the patient and to delineate a target, such as a tumor. In some embodiments, the delineation of one or more OARs, such as healthy tissue surrounding the tumor or in close proximity to the tumor may be required. Therefore, segmentation of the OAR may be performed when the OAR is close to the target tumor. In addition, if the target tumor is close to the OAR prostate in near proximity to the bladder and rectum), then by segmenting the OAR from the tumor, the radiotherapy system 100 may study the dose distribution not only in the target but also in the OAR.

In order to delineate a. target organ or a target tumor from the OAR, medical images, such as MRI images, CT images, PET images, fMRI images, X-ray images, ultrasound images, radiotherapy portal images, SPECT images, and the like of the patient undergoing radiotherapy may be obtained non-invasively by the image acquisition device 132 to reveal the internal structure of a body part, Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy and low irradiation of the OAR(s) (e.g., the OAR(s) receives as low a radiation dose as possible). Other parameters that may be considered include the location of the target organ and the target tumor, the location of the OAR, and the movement of the target in relation to the OAR, For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as Monaco® manufactured by Elekta AB of Sweden) or automatically (:.g., using a program such as the Atlas-based auto-segmentation software, ABAS™ manufactured by Elekta AB of Sweden). In certain embodiments, the 3D structure of a target tumor or an OAR may be generated automatically by the treatment planning software.

After the target tumor and the OAR(s) have been located and. delineated, a dosimetrist, physician, or healthcare, worker may determine, a dose of radiation to be applied to the target, tumor, as well a.s any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc,), margins around the target tumor and OARS, beam angle selection, collimator settings, and beam-on times. During the inverse-planning process, the physician may define close constraint parameters that set bounds on how much radiation an OAR may receive (e.g,, defining full dose to the tumor target and zero dose to any OAR; defining 95% of dose to the target tumor; defining that the spinal cord, brain stem, and optic structures receive ≤45 Gy, ≤55 Gy and ≤54 Gy, respectively). The result of inverse planning may constitute a radiation therapy treatment plan 142 that may be stored in memory 116 or database 124. Some of these treatment parameters may be correlated. For example, tuning, one parameter (e.g., weights for different objectives, such as increasing the dose to the target tumor) in an attempt to change the treatment plan may affect at least one other parameter, which in turn may result in the development of a different treatment plan. Thus, the data processing device 112 can generate a. tailored radiation therapy treatment plan 142 having these parameters in order for the radiation therapy device 130 to provide radiotherapy treatment to the patient.

In addition, the radiotherapy system 100 may include a display device 134 and a user interface 136. The display device 134 may include one or more display screens that display medical images, interface information, treatment planning parameters projection images, graphical aperture images, contours, dosages, beam angles, etc.) treatment plans, a target, localizing a target and/or tracking a target, or any related information to the user. The user interface 136 may be a keyboard, a keypad, a touch screen or any type of device that a user may input information to radiotherapy system 100. Alternatively, the display device 134 and the user interface 136 may be integrated into a. device such as a tablet computer (e.g., Apple iPad®, Lenovo Thinkpad®, Samsung Galaxy®, etc.).

Furthermore, any and all components of the radiotherapy system 100 may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the data processing device 112, the GIS 128, the image acquisition device 132 could be implemented as a virtual machine. Given the processing power, memory, and computational capability available, the entire radiotherapy system 100 could be implemented as a virtual machine.

Figure 2A:
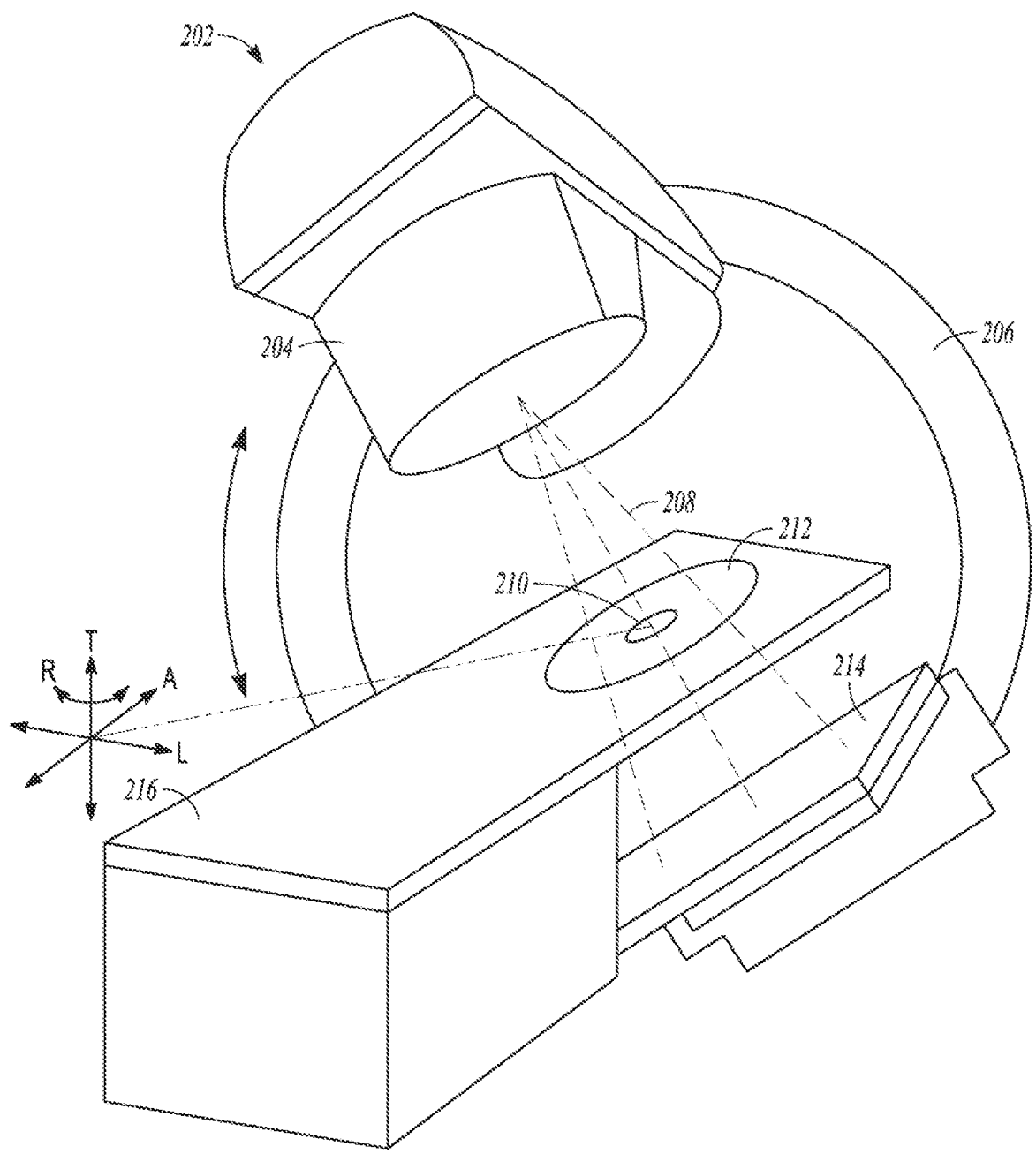
FIG. 2A illustrates an exemplary radiotherapy system that can provide a therapy beam.

FIG. 2A illustrates an exemplary radiation therapy device 202 that may include a radiation source (e.g., an X-ray source or a linac), a couch 21.6, an imaging detector 214, and a radiation therapy output 204. The radiation therapy device 202 may be configured to emit a radiation beam 208 to provide therapy to a. patient. The radiation therapy output 204 can include one or more attenuators or collimators, such as an MLC. An MLC can leaf banks each consisting of multiple MLC leaves. The leaf banks can be mounted on respective DLGs that enable rapid movement of the MLC leaves, such that the radiation therapy beam can he shaped and directed to the specified target. locus on the patient. Examples of the MLC and the DLG are discussed below, such as with reference to FIGS. 3-5.

A patient can be positioned in a region 212 and supported by the couch 216 to receive a radiation therapy dose, according to a radiation therapy treatment plan. The radiation therapy output. 204 can be mounted or attached to a gantry 206 30 or other mechanical support. One or more chassis motors (not shown) may rotate the gantry 206 and the radiation therapy output 204 around the couch 216 when the couch 216 is inserted into the treatment area. in an embodiment, the gantry 206 may he continuously rotatable around the couch 216 when the couch 216 is inserted into the treatment area. In another embodiment, the gantry 206 may rotate to a predetermined position when the couch 216 is inserted into the treatment area. For example, the gantry 206 can he configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly 10 position the patient in or out of the radiation beam 208 according to a radiation therapy treatment plan. Both the couch 216 and the gantry 206 are independently moveable from one another in multiple degrees of freedom. which allows the patient to be positioned such that the radiation beam 208 can target the tumor precisely. The MLC may be integrated with the gantry 206 to deliver the radiation beam 208 of a certain shape.

The coordinate system (including axes A, T, and L) shown in FIG. 2A can have an origin located at an isocenter 210. The isocenter can be defined as a location where the central axis of the radiation beam 208 intersects the origin of a coordinate axis, such as to deliver a prescribed radiation dose to a location on or within a patient, Alternatively, the isocenter 210 can be defined a.s a location where the central axis of the radiation beam 208 intersects the patient for various rotational positions of the radiation therapy output 204 as positioned by the gantry 206 around the axis A. As discussed herein, the gantry angle corresponds to the position of gantry 206 relative to axis A, although any other axis or combination of axes can be referenced and used to determine the gantry angle.

The gantry 206 may have an attached imaging detector 214 that is preferably opposite the radiation therapy output 204. In an embodiment, the imaging detector 214 can be located within a field of the therapy beam 208. The imaging detector 214 can maintain alignment with the therapy beam 208. The imaging detector 214 can rotate about the rotational axis as the gantry 206 rotates. In an embodiment, the imaging detector 214 can be a flat panel detector (e.g., direct detector or a scintillator detector). In this manner, the imaging detector 214 can be used to monitor the therapy beam 208 or the imaging detector 214 can be used for imaging the patient's anatomy, such as portal imaging. The control circuitry of radiotherapy device 202 may be integrated within system 100 or remote from it.

In an illustrative embodiment, one or more of the couch 216, the therapy output 204, or the gantry 206 can be automatically positioned, and the therapy output 204 can establish the therapy beam 208 according to a specified dose for a particular therapy delivery instance. A sequence of therapy deliveries can he specified according to a radiation therapy treatment plan, such as using one or more different orientations or locations of the gantry 206, the couch 216, or the 10 therapy output 204. The therapy deliveries can occur sequentially, but can intersect in a desired therapy locus on or within the patient, such as at the isocenter 210. A prescribed dose of radiation therapy can thereby be delivered to the therapy locus while damage to tissue near the therapy locus can be reduced or avoided.

Figure 2B:
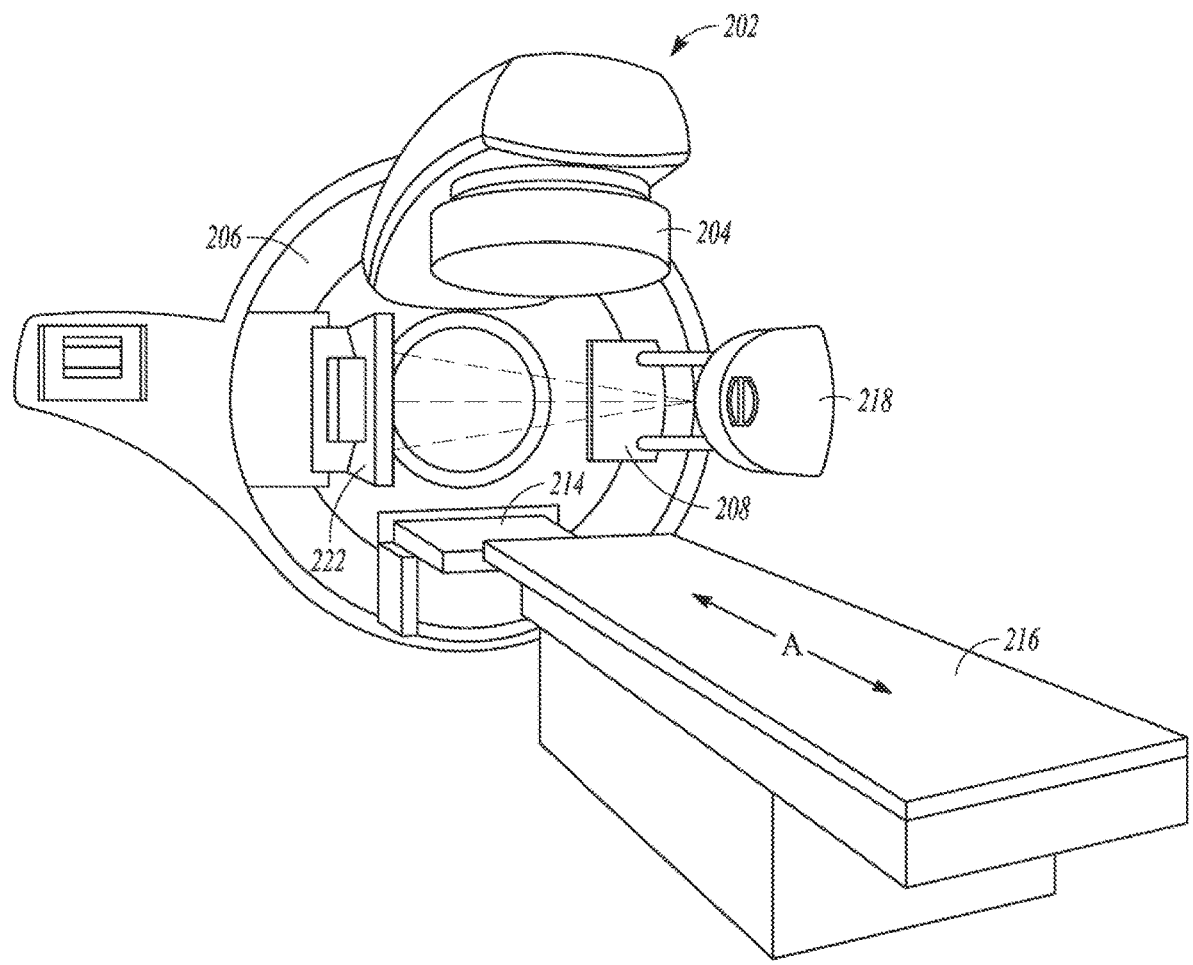
FIG. 2B illustrates an exemplary combined system including a computed tomography (CT) imaging system and a radiation therapy system.

FIG. 2B illustrates an exemplary radiation therapy device 202 that combines a radiation system (e.g., a linac) and a CT imaging system. The radiation therapy device 202 can include an WE (not shown), The CT imaging system can include an imaging X-ray source 218, such as providing X-ray energy in a kiloelectron-Volt (keV) energy range. The imaging X-ray source 218 can provide a fan-shaped and/or a conical beam 208 directed to an imaging detector 222, such as a flat panel detector. The radiation therapy device 202 can be similar to the system described in relation to FIG. 2A, such as including a radiation therapy output 204, a gantry 206, a couch 216, and another imaging detector 214 (such as a flat panel detector). The .X-ray source 218 can provide a comparatively-lower-energy X-ray diagnostic beam, for imaging.

Figure 3:
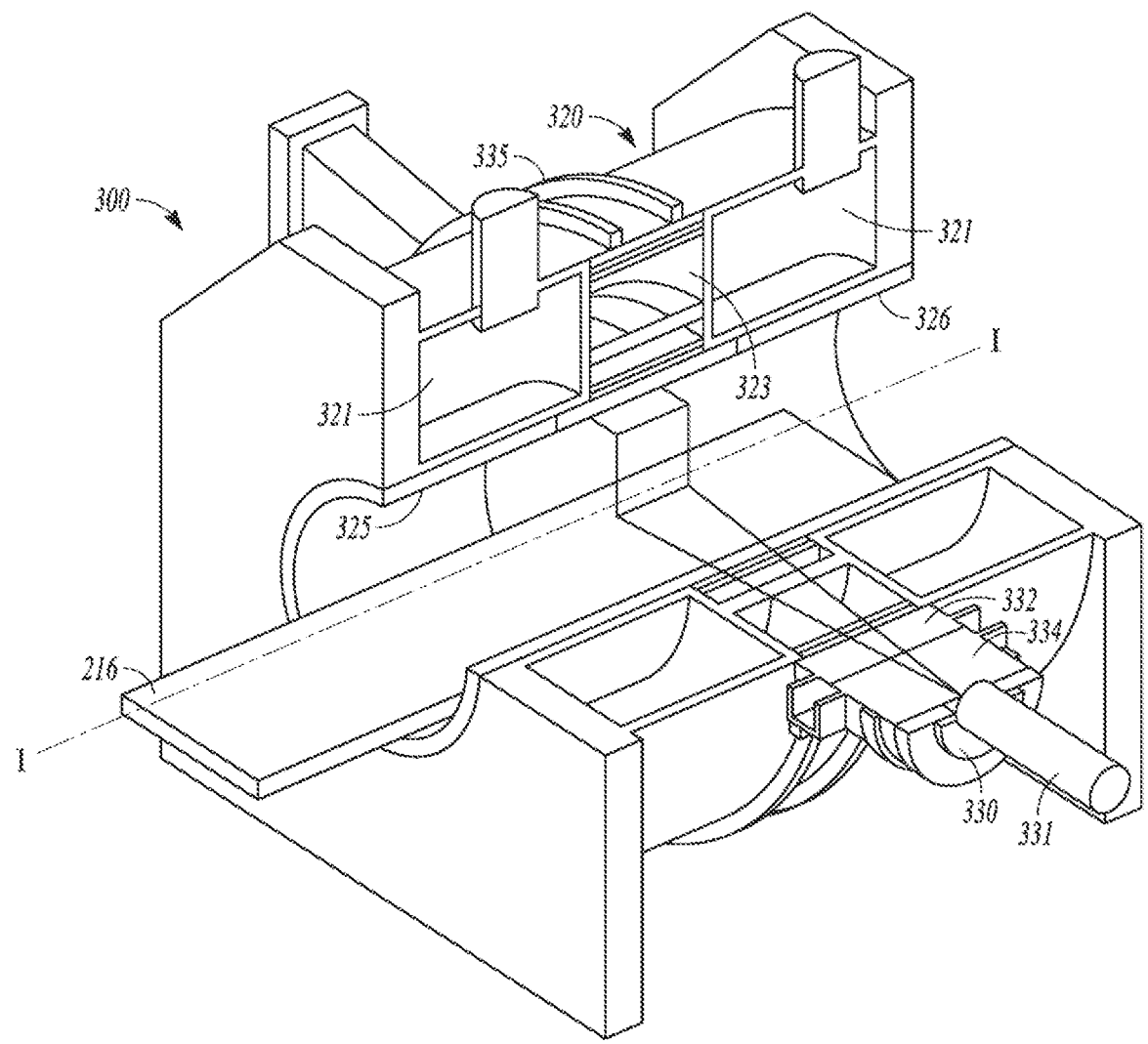
FIG. 3 illustrates a partially cut-away view of an exemplary combined system including a nuclear magnetic resonance (MR) imaging system and a radiation therapy system.

As illustrated in FIG. 213. the radiation therapy output 204 and the X-ray source 218 can be mounted on the same rotating gantry 206, rotationally-separated from each other by 90 degrees. In some examples, two or more X-ray sources can be mounted along the circumference of the gantry 206, such that each has its own detector arrangement to provide multiple angles of diagnostic imaging concurrently. Similarly, multiple radiation therapy outputs 204 can be provided, FIG. 3 illustrates an exemplary radiation therapy system 300 that combines a radiation system (e.g., a linac) and a nuclear MR imaging system, also referred to as an MR-linac system. Such a combined system is also referred to as an MR-linac system. The system 300 may include a couch 216, an image acquisition device 320, and a radiation delivery device 330. The system 300 can deliver radiation therapy to a patient in accordance with a radiotherapy treatment plan, such as the treatment plan 142 created and stored in the memory 116. In some embodiments, image acquisition device 320 may correspond to image acquisition device 132 in FIG. 1 that may acquire images of a first modality (e.g., and MIR image) or destination images of a second modality (e.g., a CT image).

The couch 216 may support a patient during a treatment session. In some implementations, the couch 216 may move along a horizontal translation axis (labeled "I"), such that the couch 216 can move the patient resting on the couch 216 into and/or out of the system 300. The couch 216 may also rotate around a central vertical axis of rotation, transverse to the translation axis. To allow such movement or rotation, the couch 216 may have motors (not shown) enabling the couch to move in various directions and to rotate along various axes. A controller (not shown) may control these movements or rotations in order to properly position the patient according to a treatment plan, In some embodiments, the image acquisition device 320 may include an MR imaging machine used to acquire 2D or 3D MI images of the patient before, during, and/or after a treatment session. The image acquisition device 320 may include a magnet 321 for generating a. primary magnetic field for magnetic resonance imaging. The magnetic field lines generated by operation of the magnet 321 may run substantially parallel to the central translation axis "I". The magnet 321 may include one or more coils with an axis that runs parallel to the translation axis "I". In some embodiments, the one or more coils in magnet 321 may be spaced such that a central window 323 of magnet 321 is free of coils. in other embodiments, the coils in magnet 321 may be thin enough or of a reduced density such that they are substantially transparent to radiation of the wavelength generated by radiotherapy device 330. In some embodiments, the image acquisition device 320 may also include one or more shielding coils, which may generate a magnetic field outside the magnet 321 of approximately equal magnitude and opposite polarity in order to cancel or reduce any magnetic field. outside of the magnet 321, As described below, a radiation source 331 of radiotherapy device 330 may be positioned in the region where the magnetic field is cancelled, at least to a first order, or reduced.

The image acquisition device 320 may also include two gradient coils 325 and 326, which may generate a gradient magnetic field that is superposed on the primary magnetic field. The coils 325 and 326 may generate a. gradient in the resultant magnetic field that allows spatial encoding of the protons so that their position can be determined. The gradient coils 325 and 326 may be positioned around a common central axis with the magnet 321 and may be displaced along that central axis. The displacement may create a gap, or window, between the coils 325 and 326. In embodiments where the magnet 321 includes a central window 323 between the coils, the two windows may be aligned with each other.

In some embodiments, image acquisition device 320 may be an imaging device other than an MRI, such as an X-ray, a CT, a CBCT, a spiral CT, a PET, a SPECT, an optical tomography, a fluorescence imaging, ultrasound imaging, radiotherapy portal imaging device, or the like, As would be recognized by one of ordinary skill in the art, the above description of image acquisition device 320 concerns certain embodiments and is not intended to be limiting.

The radiotherapy device 330 may include the radiation source 331 (e.g., an X-ray source or a linac), and a collimator such as an MLC 332, A collimator is a beam-limiting device that can help to shape the beam of radiation emerging from the machine and can limit the maximum field size of a beam. The MLC 332 can be used for shaping, directing, or modulating an intensity of a radiation therapy beam to the specified target locus within the patient. The MLC 332 can include metal collimator plates also known as MLC leaves, which slide into place to form the desired field shape. The leaf banks can be mounted on respective DLGs 334 that enable rapid movement of the MLC leaves. The radiotherapy device 330 may be mounted on a chassis 335. One or more chassis motors (not shown) may rotate Chassis 335 around the couch 216 when the couch 216 is inserted into the treatment area. In an embodiment, chassis 335 may be continuously rotatable around the couch 216, when the couch 216 is inserted into the treatment area. Chassis 335 may also have an attached radiation detector (not shown), preferably located opposite to radiation source 331 and with the rotational axis of chassis 335 positioned between radiation source 331 and the detector. Further, device 330 may include, control circuitry (not shown) used to control, for example, one or more of the couch 216. image acquisition device 320, and radiotherapy device 330. The control circuitry of radiotherapy device 330 may be integrated within system 300 or remote from it.

During a radiotherapy treatment session, a patient may be positioned on the couch 216. System 300 may then move the couch 216 into the treatment area defined by magnetic 321 and coils 325, 326, and chassis 335. Control circuitry may then control radiation source 331, MLC 332, and the chassis motor(s) to deliver radiation to the patient through the window between coils 325 and 326 according to a radiotherapy treatment plan.

The radiation therapy output configurations illustrated in FIGS. 2A-2B and 3, such as the configurations where a radiation therapy output can be rotated around a central axis (e.g., an axis "A"), are for the purpose of illustration and not limitation. Other radiation therapy output configurations can he used. For example, a radiation therapy output can be mounted to a robotic arm or manipulator having multiple degrees of freedom, In yet another embodiment, the therapy output can be fixed, such as located in a region laterally separated from the patient, and a platform supporting the patient can be used to align a radiation therapy isocenter with a specified target locus within the patient.

Figure 4:
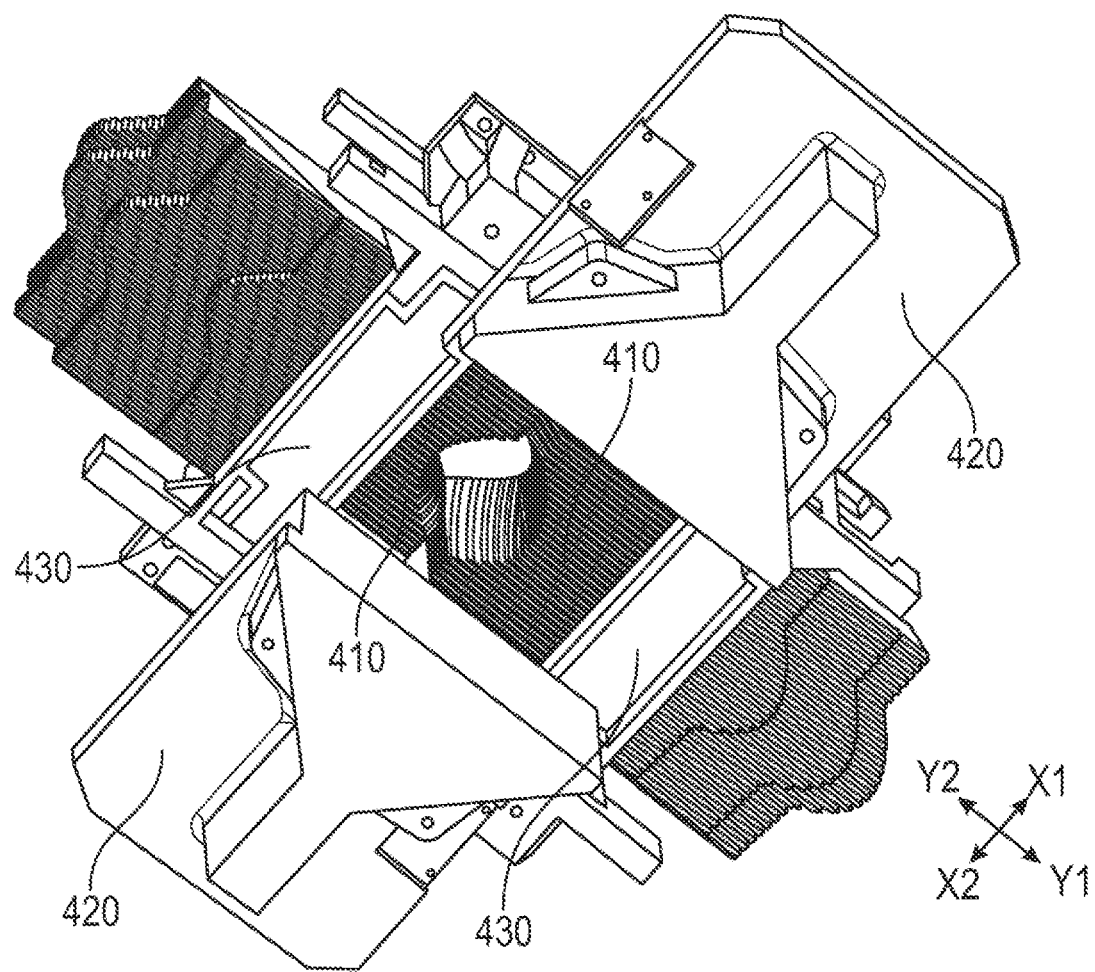
FIG. 4 is a diagram illustrating an exemplary collimator that can be used in radiotherapy system such as an IVIR-linac machine.

FIG. 4 is a diagram illustrating an exemplary collimator 400 that can be used in a radiotherapy system, such as an MR-linac machine. An example of the collimator is Agility™ collimator (Elekta AB, Sweden). The collimator 400 can include, beam shaping components including MLC leaves 410, diaphrams 420, and DLGs 430. The MLC leaves 410, which are embodiments of the MLC leaves 332, 25 can consist of an array of metal collimator plates, known as MLC leaves. The MLC leaves can have curved leaf tips. In an example, the MLC leaves may be made of tungsten alloy. The MLC leaves may be arranged into two separate MLC leaf banks. In an example, an MLC can include 160 leaves arranged into leaf banks of 80 leaves each. Each bank of MLC leaves is contained within, and mounted on, a respective DLG 430. The DLG 430, which is an embodiment of the DLG 334, can move with the MLC leaves 410 in a direction (Y direction, along Y1 or Y2 axis as shown in HG. 4) parallel to the arrangement of MLC leaves. FIG. 4 illustrates a first leaf hank contained in a first DLG. and a second leaf bank positioned opposite of the first leaf hank and contained in a second DLG. The MLC leaves in the first hank can move in Y1 axis, and the MLC leaves in the second bank can move in Y2 axis opposite of the Y1 axis. The first DLG is referred to as DLG-Y1, and the second DLG is referred to as DLG-Y2. Through simultaneous leaf and DLG movement, rapid MLC movement and efficient beam shaping can he achieved. In a non-limiting example, the maximum velocity of the MLC leaves 410 is approximately 35 millimeter per second (minis), and the maximum velocity of the DLG 420 is approximately 30 mm/s. Therefore, when the DLG 420 and the MLC leaves 410 are moving in the same direction, the maximum possible leaf velocity can he approximately 65 film's. in a non-limiting example, the maximum travel of a MLC leaf within the DLG 420 can he approximately 200 mm, and the DLG has an approximately 150 mm range of travel (measured at the isocenter). Thus, the maximum overtravel of the leaves can be approximately 150 mm.

A pair of sculpted diaphragms 420 (also referred to as jaws) can he mounted orthogonally to the MLC leaves 410. In an example, the diaphragms 420 can over-travel the central axis by a specific distance, such as up to 150 mm in a non-limiting example. The diaphragms 420 can move in a direction (X direction) perpendicular to the direction of MLC leaf travel (Y direction). As illustrated in FIG. 4, a fist diaphragm can move in X1 axis. and a second diaphragm can move in X2 axis opposite of the X1 axis. In example, the diaphragms 420 can have a maximum velocity of approximately 90 mm/s. The diaphragms can have rounded radiation defining edge. Both the MLC leaves 410 and the diaphragms 420 have rounded ends. In some examples, the diaphragms 420 can have "thick" regions providing full attenuation and "thin" regions where attenuation is provided by both the leaves and the diaphragm.

The DLG 420 may be coupled to a DLG driving system comprising an electric motor, power transmission, brakes, among other components that drive the DLG 420 at desired speed and direction. A controller can be coupled to the driving system to control the motion of the DLG 420. As discussed previously, the DLGs, like other high-speed moving components in a machine, may subject to faults and failure. These faults may he associated with one or more components of the DLG driving system or the control system, such as the motor, the transmission, one or more brakes, a linear slide to support the DIX; in motion, or a coupling, unit that connects different components. Timely and accurate detection (including early detection or prediction) and diagnosis of these faults may be important to ensure proper system operation and accurate radiotherapy delivery to the patient. Various embodiments as discussed in this document, including deep learning-based FDD as discussed with reference to FIGS. 6A-6C and 7-8, can improve the predictive maintenance of a radiotherapy equipment.

Figure 5:
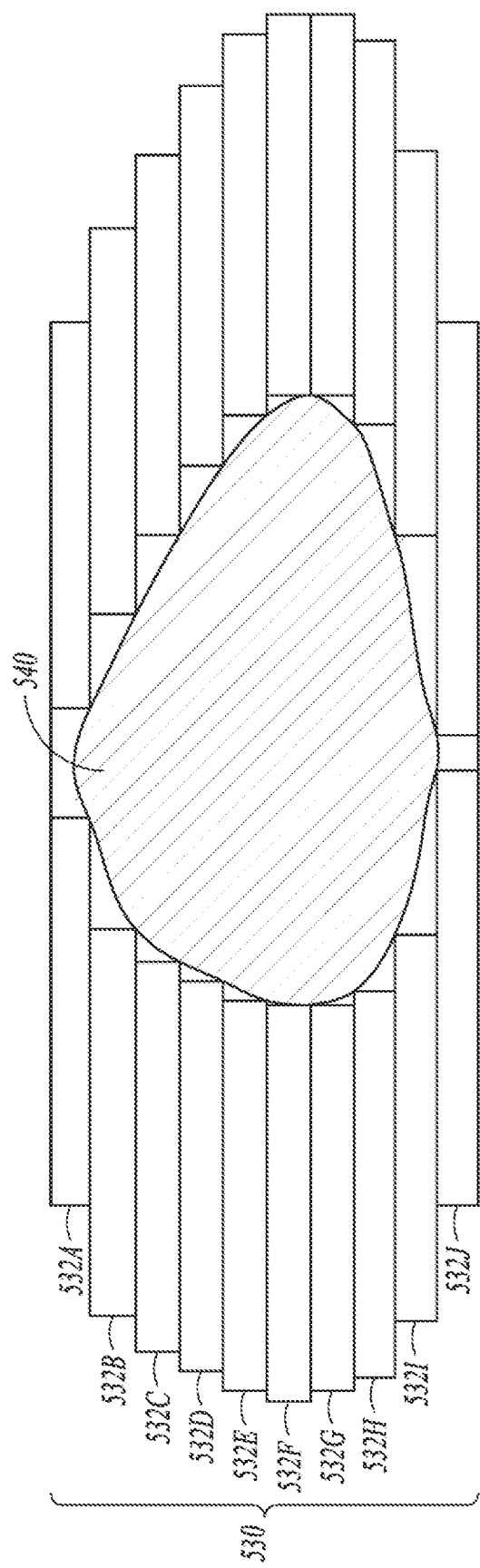
FIG. 5 is a diagram illustrating an exemplary MLC and part of the environment in which it can be used.

FIG. 5 illustrates an exemplary MLC 530, and part of the environment in which it can be used. The MLC 530 can be an embodiment of the MLC 430 or the MLC 232. The MLC 530 can include, h way of example and not limitation, leaves 532A-532J that can he automatically positioned to define an aperture approximating a tumor 540 cross section or projection. The leaves 532A through 532J permit modulation of the radiation therapy beam. The leaves 532A through 532J can be made of a material specified to attenuate or block the radiation beam in regions other than the aperture, in accordance with the radiation treatment plan. For example, the leaves 532A through 532J can include metallic plates, such as comprising tungsten, with a long axis of the plates oriented parallel to a beam direction and having ends oriented orthogonally to the beam direction (as shown in the plane of the illustration of FIG. 2A). A "state" of the MLC 332 can be adjusted adaptively during a course of radiation therapy treatment, such a.s to establish a therapy beam that better approximates a shape or .location of the tumor 540 or other target locus. This is in comparison to using a static collimator configuration or as compared to using an MLC 332 configuration determined exclusively using an "offline" therapy planning technique. A radiation therapy technique using the MLC 332 to produce a specified radiation dose distribution to a tumor or to specific areas within a tumor can be referred to as JMRT. The resulting beam shape that is output using the MLC 332 is represented as a graphical aperture image. Namely, a given graphical aperture image is generated to represent how a beam looks (beam shape) and its intensity after being passed through and output by MLC 332.

Figure 6A:
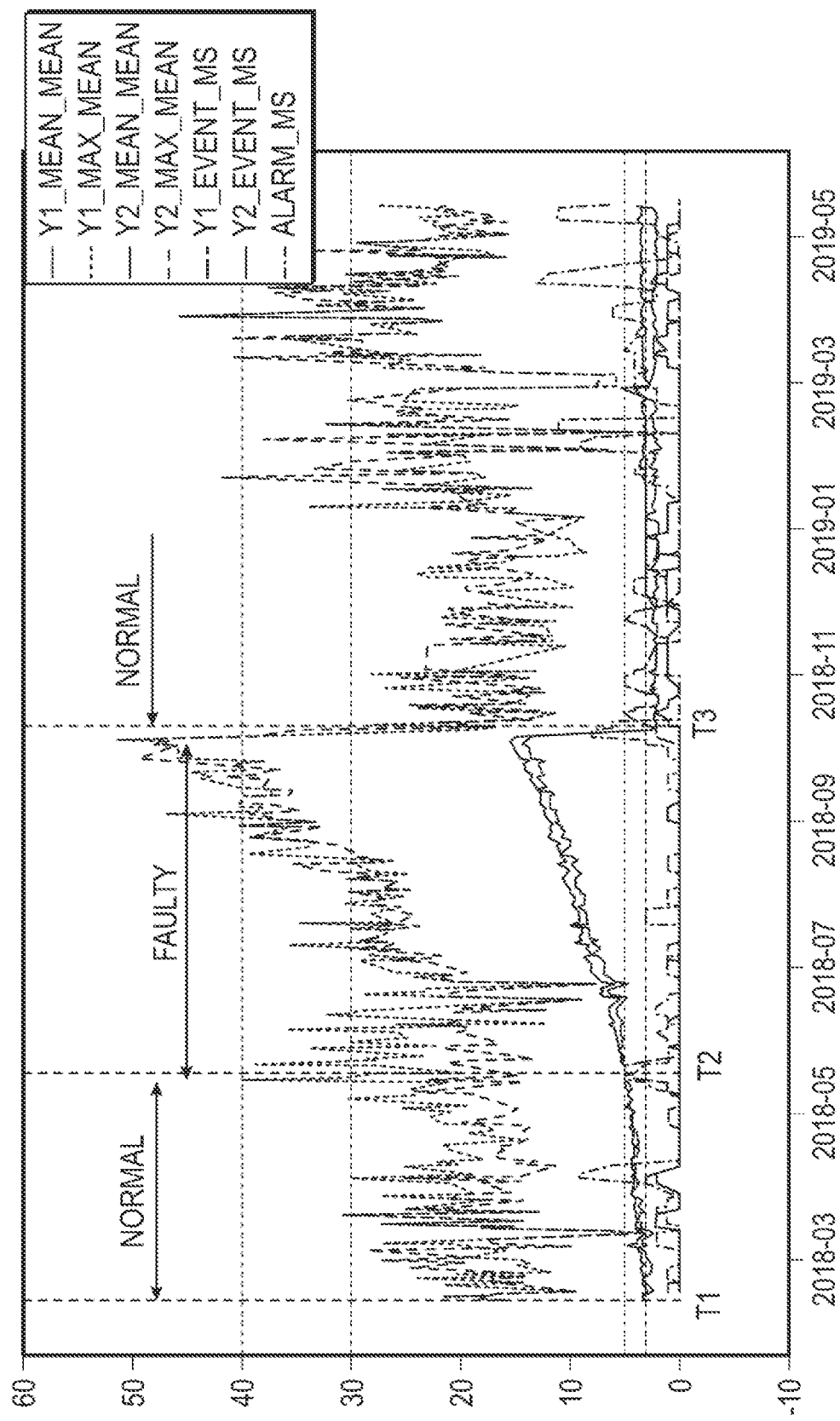
FIGS. 6A-6C are diagrams illustrating trends of machine data collected from DLGs of various NIR-linac systems before, during, and after correction of a DLG fault.
Figure 6B:
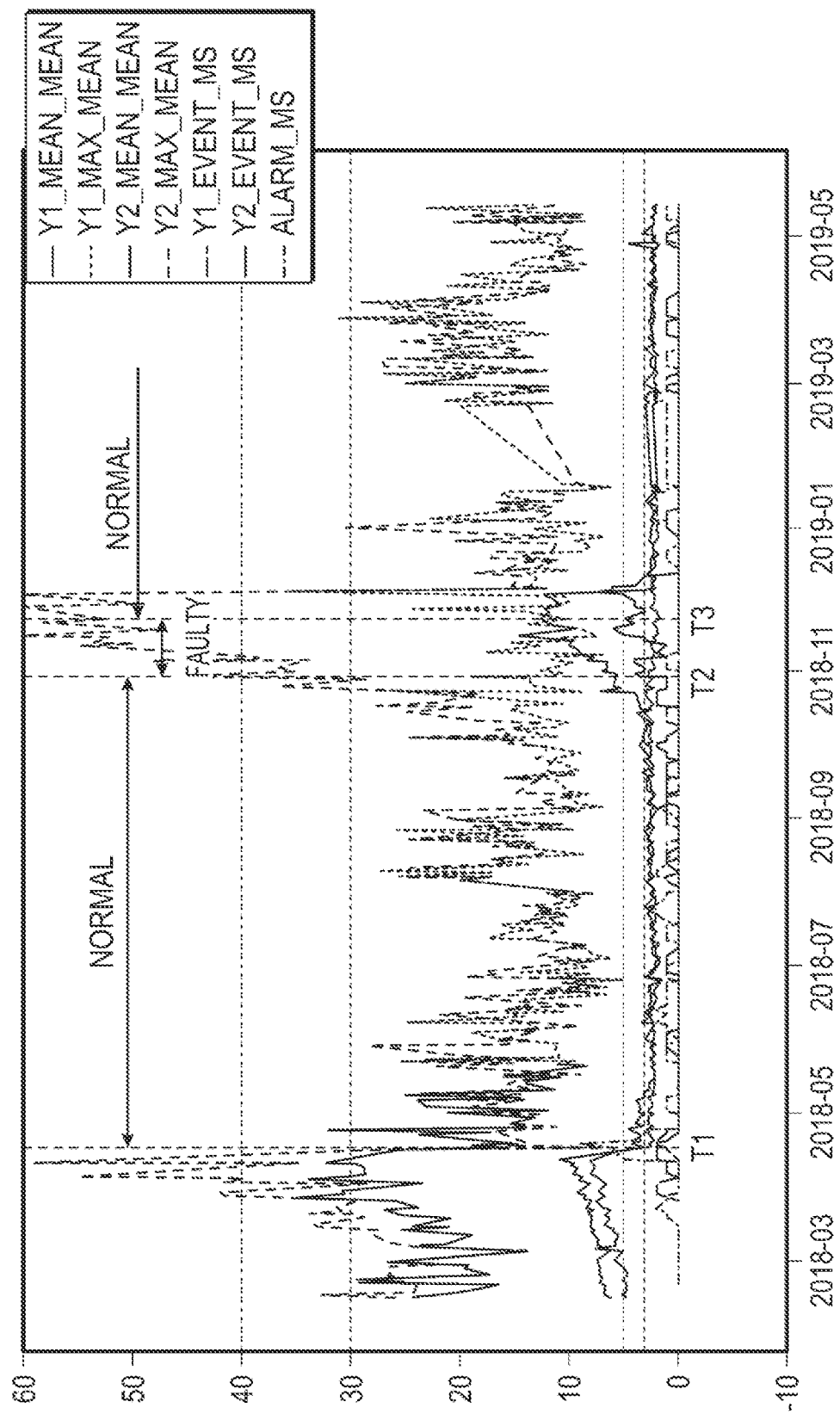
Figure 6C:
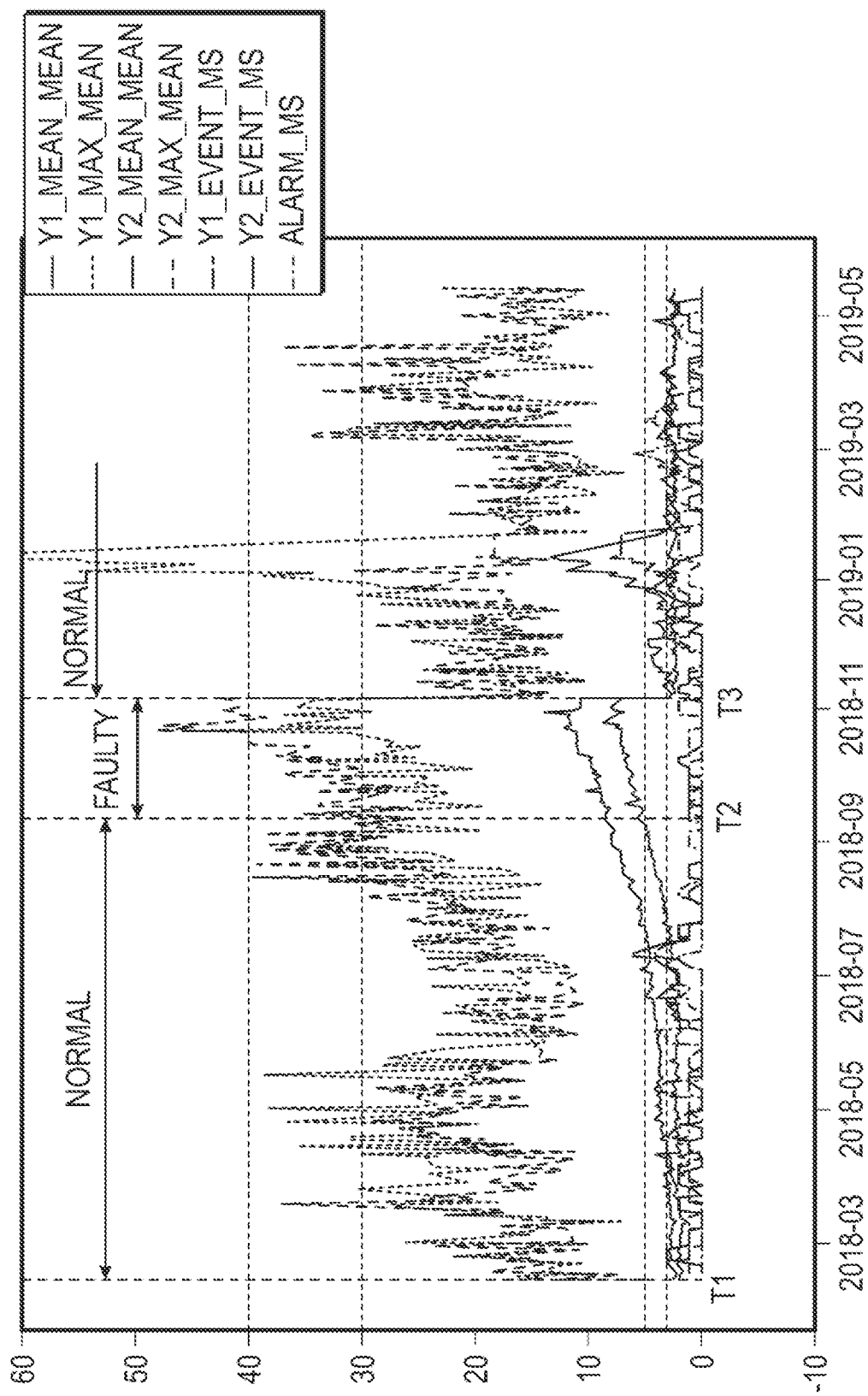

FIGS. 6A-6C are diagrams illustrating exemplary trends of machine data collected from DI s of various MR-linac systems before and during a DLG fault, and after said DLG fault has been corrected. Different types of DLG faults are considered in these examples. The machine data may include sequences of measurements of a physical parameter over a specified time period. The measurements may be taken from one or more parts of the DLG driving system or the control system, such as an electric motor, a power transmission, a brake, a linear slide, or a coupling unit connecting different components.

In an example, the measured DLG data may include DLG electric current measurements when the collimator is in active operation. The electric current may be measured from one or more DLGs at respective Y1 or Y2 axes (e.g., the DLG-Y1 or DLG-Y2 as illustrated in FIG. 4), denoted by $I_{y1}$ and $I_{y2}$, respectively. The DLG electric current $I_{y1}$ and $I_{y2}$ can have floating-point values.

In another example, the DLG data may include positions of one or more of DLG-Y1 or DLG-Y2. The position data can be represented by numerical coordinates, or a categorical indicator of a DLG out-of-position event indicating that a DLG (e.g., DLG-Y1, or DLG-Y2) fails to achieve a specified speed when it moves to a preset position. In an example, the DLG data may include a count of out-of-position events associated with DLG-Y1 or associated with DLG-Y2, denoted by $NP_{y1}$ and $NP_{y2}$, respectively, that have occurred within a specified time period. The out-of-position event counts $NP_{y1}$ and $NP_{y2}$ can have integer values.

In yet another example, the DLG data may include alarms triggered by one or more alarm events, or a count of alarms during a specified time period, denoted by N_Alarm. The alarm count N_Alarm can have integer values. By way of example and not limitation, the alarm events may include: (1) a "terminated MLC error alarm", which is a generic MLC termination alarm that can be triggered by many components of a collimator including the DLG; (2) a "terminated MLC Not OK alarm", corresponding to an unexpected termination of treatment such as due to incorrect position of DLG, oscillation, or other issues; (3) an "MLC Lost Leaf reflector alarm", which can occur when the DLGs are driving too slow or fast, such that the leaf reflectors of the individual leaves may not be in an expected position, and the leaf reflectors are lost and later found many times in a short period of time; (4) a "reflectors not calibrated alarm" which may occur when positions of one or more reference reflectors have been lost, such that calibration of the reflectors as a minimum is required; (5) a "terminated DLG-Y1 position alarm" indicating a termination of DLG-Y1; or (6) a "terminated DLG-Y2 position alarm" indicating a termination of DLG-Y2.

The DLG data as discussed above may be acquired continuously, periodically, or according to a specified data acquisition schedule. In some examples, statistical metrics (e.g., mean, median, maximum (max), minimum (min), range, variance, standard deviation (SD), or other higher-order statistics) or cumulative metrics (e,g,, sum, moving-sum, or moving-average) may be generated from the DLG electric current measurements, DLG out-of-position event counts, or alarm counts. By way of example and not limitations, one or more metrics may be generated from the DLG current measurements, hereinafter referred to as DLG current metrics. Examples of the DLG current metrics may include one or more of: (1) hourly current metrics such as hourly mean $I_{y1}$ or hourly mean $I_{y2}$, or hourly max $T_{y1}$ or hourly max $I_{y2}$; or (2) daily current metrics such as daily mean, daily max, or daily SD of $I_{y1}$ or $I_{y2}$. In an example, at least some daily current metrics (e.g., daily mean, max, or SD of $I_{y1}$ or of $I_{y2}$ may be computed using hourly mean current measured over a number of hours up to 24 hours. In another example, at least some daily current metrics (e.g., daily mean, max, or SD of $I_{y1}$ or of $I_{y2}$) may be computed using hourly max current measured over a specified number of hours up to 24 hours. In some examples, the DLG metrics may include a moving-average of daily current metrics, computed over a moving time window of a specified number of days (e.g., a 5-day moving window). Examples of the moving-average current metrics may include a moving-average of daily mean current, where the daily mean current may be determined based on hourly mean current, or based on hourly max current, over a specified number of hours up to 24 hours, Each of the hourly current metrics, the daily current nip ti or the moving-average of daily current metrics may he computed respectively for DLG-Y1 (e.g., based on hourly $I_{y1}$) or DLG-Y2 (e.g., based on hourly $I_{y2}$).

In addition to the statistical DLG current metrics, metrics of DLG out-of-position event counts may be computed. Examples of the DLG out-of-position event metrics may include one or more of: (1) a daily count $NP_{y1}$ or a daily count $NP_{y2}$, over a number of hours up to 24 hours; (2) a moving-sum of $NP_{y1}$, or a moving-sum of $NP_{y2}$, over a moving time window of a specified number of days (e.g., a 5-day moving window); or (3) a moving-average of $NP_{y1}$ or a moving-average of $NP_{y2}$, over a moving time window of a specified number of days (e.g., a 5-day moving window). Additionally or alternatively, metrics of DLG alarm counts may be computed, which may include., by way of example and not limitation, one or more of: (1) a daily count of alarms (N_Alarm) over a number of hours up to 24 hours; (2) a moving-sum of N_Alarm over a moving time window of a specified number of days (e.g., a 5-day moving window); or (3) a moving-average of N_Alarm over a moving time window of a specified number of days (e.g., a 5-day moving window). The daily count, moving-sum, or moving-average of alarm counts may be computed respectively for one or more types of alarm events as discussed above. Alternatively or additionally, the daily count, moving-sum, or moving-average of alarm counts may be computed across all alarm events irrespective of alarm type.

FIGS. 6A-6C each illustrates exemplary trends of a plurality of DLG metrics. By way of example and not limitation, these data trends may include: daily mean current $I_{y1}$ (Y1_mean_mean); daily max current $I_{y1}$ (Y1_max_mean, the average of hourly max current $I_{y1}$ within a day); daily mean current $I_{y2}$ (Y2_Mean_mean); daily max current $I_{y2}$ (Y2_max_mean, the average of hourly max current $I_{y2}$ within a day); moving-sum of Y1 out-of-position event count $NP_{y1}$ over a 5-day moving window (Y1_event_MS); moving-sum of Y2 out-of-position event count $NP_{y2}$ over a 5-day moving window (Y2_event_MS); and moving-sum of alarm count N_Alarm over a 5-day moving window (Alarm_MS). In each of these figures, T1 represents the time of initiating a predictive maintenance session for predicting, or detecting early signs of, a DLG fault. T2 represents the time of an onset of an identified (e.g., by a human expert) fault type, and T3 represents the time when said fault type is corrected or resolved. As such, a fault prediction window can be defined between T1 and T2, and fault is present in a window defined between T2 and T3.

FIG. 6A illustrates the trends of the DLG metrics corresponding to a fault associated with a printed circuit board (PCB) of the DLG ("PCB fault"). in this example, the PCB fault is accompanied by elevation over time of the four DLG current metrics (Y1_mean_mean, Y1_max_mean, Y2_mean_mean, and Y2_max_mean) between T2 and T3. Correction of the PCB fault is accompanied by fallback of the four DLG current metrics following T3. Among other metrics, daily mean current at Y1 and Y2 (Y1_mean_mean and Y2_mean_mean) both increase prior to the onset of the PCB fault, suggesting the power of these metrics in predicting the PCB fault of this type.

FIG. 6B illustrates the trends of the DLG metrics corresponding to a fault associated with DLG brakes ("brake fault"). in this example, between T2 and T3, the brake fault is accompanied by more prominent elevation over time of the metrics associated with Y2 (Y2_mean_mean, Y2_max_mean, and Y2_event_MS) than the metrics associated with Y1. Correction of the brake fault is accompanied by fallback of said metrics associated with Y2 following T3. Said metrics associated with Y2 also increase prior to the onset of the brake fault, suggesting the power of these metrics in predicting the brake fault of this type.

FIG. 6C illustrates the trends of the DLG metrics corresponding to a hybrid fault involving both the PCB and the DLG brakes. In this example, the hybrid fault is accompanied by elevation over time of the four DLG current metrics (Y1_mean_mean, Y1_max_mean, Y2_mean_mean, and Y2_max_mean) between T2 and T3. Correction of the hybrid fault is accompanied by fallback of the four DLG current metrics following T3. Among other metrics, said four DLG current metrics all increase prior to the onset of the hybrid fault, suggesting the power of these metrics in predicting the hybrid fault of this type.

Figure 7A:
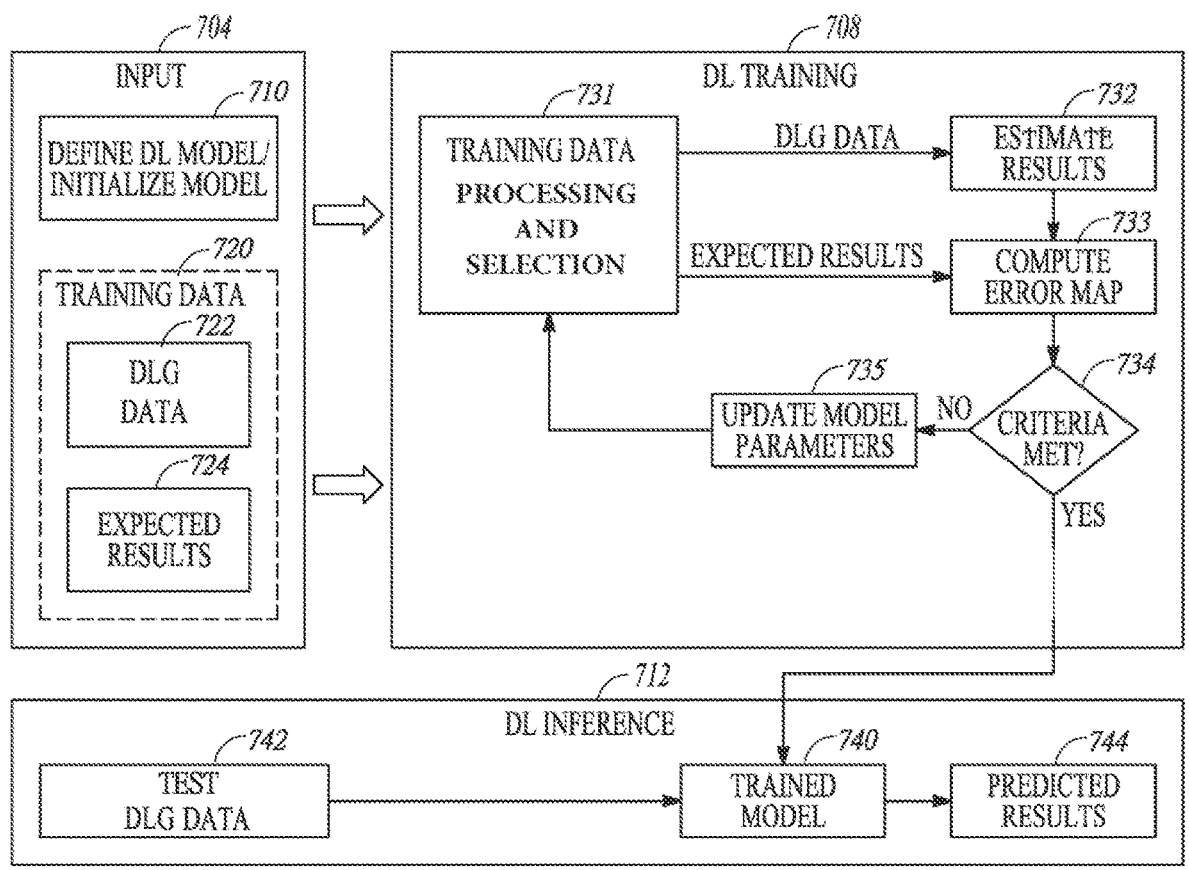
FIG. 7A is a block diagram illustrating an exemplary process for training an FDD deep learning model, and using the trained model to detect and diagnose a DLG fault in a target radiotherapy system.

FIG. 7A is a. diagram illustrating an exemplary process 700A for training an FDD deep learning (DL) model (or a machine-learning model), and using the (rained FDD model to detect and diagnose a fault associated with one or more components in radiotherapy system, such as a DLG in a linac system. The process 700A can be implemented as computer-readable. and executable instructions, such as part of the FDD software package 147, stored in the memory 116 of the radiotherapy system 100. Inputs 704 can include a specific deep learning model 710 having an initial set of values, and training data 720. Examples of the deep learning model 710 can include a convolutional neural network (CNN), a recurrent neural network (RNN), a deep belief network (DBN), or a hybrid neural network comprising two or more neural network models of different types or different model configurations.

Referring now to FIG. 7B, a CNN 700B can be constructed and used in the process 700A. A CNN network can automatically learn the characteristics of data from samples, eliminating the complex feature extraction in conventional machine learning models which generally requires substantial expert knowledge. Additional advantage of the CNN is that by means of weight sharing, the scale of CNN parameters can be greatly reduced. As a result, the complexity of the training process can he reduce, the converging speed can he increased, and the model generalization ability can be enhanced.

By way of example and not limitation, the CNN 700B as illustrated in FIG. 7B can include one input layer 751, intermediate learning layers 752, and a dense layer 753 that forms a fully connected output layer. In the illustrated example, the intermediate learning layers 752 comprises four convolutional layers (e.g., four one-dimensional convolutional layer, or "CONV1D" as shown) and one global average pooling layer. The global average pooling layer can reduce the weight parameters of the network and reduce the training complexity. A batch normalization (BN) operation can be carried out after each convolution layer. In some examples, a non-linear activation layer can be used in each intermediate layer. An example of the activation function is a rectified linear unit (ReLU), The EN layer can improve the gradient flowing through the network, solve the problem of gradient disappearance, allow greater learning rate, improve training speed, reduce the strong dependence on initialization, improve regularization strategy, reduce the need for dropout, and effectively improve the generalization ability of the CNN network.

Referring now to FIG. 7C, an RNN can be constructed and used in the process 700A. An RNN include connections between nodes to form a directed graph along a temporal sequence. It can use internal state (memory) to store past information, and the network decisions are influenced by what it has learnt from the past. This makes RNN suitable to process sequences of inputs. In an example, a long short-term memory (LSTM) network can be used. The LSTM is a. type of RNN architecture, characterized by feedback connections. A common LSTM unit can be composed of a. cell, an input gate to decide how much new information is to be added to the cell, a forget gate to decide what information is to be discarded or preserved in the cell, and an output gate to decide the values to output, The LSTM cell can remember values over arbitrary time intervals, and the three gates can regulate the flow of information into and out of the cell, which makes LSTM network particularly suited to sequential learning and pattern recognition (e.g., processing, classifying, and making predictions based on entire sequences of data, such as time series data).

By way of example and not limitation, FIG. 7C illustrates an LSTM 5 network 700C that can include one input layer 761, intermediate learning layers 762, and a dense layer 763 which can be a fully connected output layer. The intermediate learning layers 762 can include two to four LSTM layers (e.g,, three LSTM layers as shown in FIG. 7C). In order to prevent over-fitting of the model, a dropout operation can be carried out after each LSTM layer. The dense layer 753 can be a fully connected output layer. In an example, L2 regularization can be implemented into the full connection layer. Regularization is a process to control the mod& complexity by adding a penalty term to the objective function (or cost function, or loss function). For L2 regularization, the penalty term is defined as an L2 norm equal to the square of the magnitude of feature weights in the neural network model. The resulting cost function can include an estimation error term (e.g., sum of squared error term) and the penalty term. The use of L2 regularization can help achieve a trained model with a preferred balance between model complexity and prediction performance can be achieved.

Referring now back to FIG, 7A, the training data 720 can include DLG data 722 and expected results 724. The DLG data 722 can be collected from DLGs in a plurality of radiotherapy systems (e.g., linac machines) including, for example, one or more normal (i.e., fault-free) DLGs and one or more faulty DLGs with identified faults. For each DLG, the corresponding DLG data 722 may contain information about configuration and operational status of the DLG. In some examples, the DLG data 722 can include one or more DLG metrics, such as one Of more statistical or cumulative, DLG current metrics, one or more of the statistical or cumulative DLG out-of-position event counts, or one or more of the statistical or cumulative, DLG alarm counts, as discussed above with reference to FIGS. 6A-6C. In some examples, values of a DLG metric may be trended over a specified time period (e,.g., 20-30 days) to form a metric sequence (e.g., a time series). Such DLG metric sequences, corresponding to a plurality of DLG metrics, can be generated respectively for normal and faulty DLGs to form the training data 720. In an example, a specified number (N) of DLG metrics (including one or more of statistical or cumulative DIX; current metrics, statistical or cumulative DLG out-of-position event counts, or statistical or cumulative DLG alarm counts as discussed above) can each be trended over a specified number (M) of days. The training data 720 can be represented by a two-dimensional (M-by-N) data matrix. Examples of constructing training dataset 720 using a DLG metric trend are discussed below, such as with reference to FIG. 9.

The expected results 724 can include designations for normal DLGs and faulty DLGs, such as fault labels representing fault presence/absence and fault types. The fault labels may be provided by a human expert. In an example, normal DLGs are labeled as "0", and the faulty DLGs each have a numerical fault label representing a fault type, such as "1" for DLG brake fault, "2" for DLG circuit board fault, "3" for a hybrid fault involving both the brake and the circuit board, "4" for a drive motor fault, "5" for a DLG linear slide fault (e.g., greasing slide), or "6" for DLG coupling fault (e.g., loose coupling), among other fault types.

The deep learning (DL) model training process 708 includes a training data preprocessing and selection module 731. The training data preprocessing, among other things, can mitigate certain deficiencies of the training data. One of such deficiencies is data imbalance between normal (fault-free) DLGs datasets (also referred to as "negative" samples) and faulty DLG datasets (also referred to as "positive" samples) in the training set 720, In an example, the negative to positive sample ratio can be 6:1 to 10:1. The data imbalance can affect the performance of a trained deep learning model in predicting, detecting, and diagnosing faults. The data preprocessing 731 may mitigate data imbalance using one or more techniques, such as under-sampling, over-sampling, changing the penalty weight of the positive and negative samples, enhancing penalty items in a cost function of the deep learning model, and model integration. in accordance with various embodiments discussed in this document, oversampling, penalty weight adjustment for positive and negative samples, and model integration are used to preprocess the training data. These techniques can preserve information in the original data as much as possible. In an example, different penalty weights are assigned to the positive and negative samples based at least on the sample size. In an example, the penalty weights can be inversely proportional to the sample size. For example, larger weights can be assigned to positives samples (corresponding to DLG faults) which generally have a smaller sample size in the training set, and smaller weights can be assigned to negative samples (corresponding to normal DLGs) which generally have a .larger sample size in the training set.

The data imbalance may additionally or alternatively be mitigated using a data enhancement process to boost the number of positive samples associated to one or more DLG faults, For example, the data enhancement process can include exchanging the DLG-Y1 data and DLG-Y2 data. associated with identified brake fault. Through data exchange, positive samples associated with brake fault can be doubled. Additionally or alternatively, Synthetic Minority Oversampling Technique (SMOTE) may be used to synthesize additional minority samples (the positive samples, or DLG data associated with identified faults) based on existing actually measured minority samples, and thus to reduce the level of data imbalance. The SMOTE thinks from the perspective of existing minority samples, and synthesizes new samples at some distance in the feature space) from them towards one of their neighbors. Clustering method can he used to generate new samples to prevent model overfitting, which may be caused by simple over-sampling of existing samples.

Another deficiency of the training data is inconsistent sample distribution between training set and other sets such as the test set, or the actual prediction set. The inconsistent data distribution may result in a trained model that, although performs well in the test set, does not provide satisfactory prediction accuracy in the actual prediction set. To overcome the inconsistency of sample distribution across different datasets, a transfer learning module can be added to the deep learning model. Transfer learning is a method where a model developed for one task is reused as the starting point for a. model On a different but related problem. Through model reuse, transfer learning can substantially speed up the model training progress and can improve the performance when modeling the second problem. According to various embodiments, transfer learning can he applied to a trained deep learning model, such as an N-layer CNN or LSTM model trained on the training data. Model parameters of the first N–layers can then be frozen, and a new dataset (e.g., a prediction set different from the training set used for training the CNN or LSTM model) can be used to the tune the parameters of only the last layer (N-th layer), which can be a full connection layer. In an example, the prediction set for training the last full connection layer can include DLG data collected at a different time (e.g., a different day) than the training data.

As illustrated in MG. 7A. the preprocessed DLG data can be fed into the deep learning model to generate estimated results 732, such as a decision of a presence or absence of a fault, or a fault type if a fault is decided to present, The estimated fault detection and diagnosis at 732 can then be compared to the expected results 724 (e.g., "0" for no fault, and non-zero numbers for different identified fault types). A difference, or estimation error, can he computed at 733. The estimation error can he compared to model convergence or training stopping 10 criteria at 734, such as proceeding to a sustained minimum for a specified number of training iterations.

If at 734 it is determined that the convergence or training stopping criteria have not been satisfied, the estimation errors can be used to update the parameters of the deep learning model (e.g., .layer node weights and biases), such as through backpropagation, to reduce or minimize errors in the machine parameter or the estimations errors during subsequent training trials. Another batch of training data can then be selected from the training data 720 and expected results for another iteration of deep learning model training.

In an embodiment, model parameter update using the estimation error may be carried out to minimize or reduce a cost function (or objective function, Of loss function), such as the cost function given in Equation (1):

$$J(\Theta^*) = \arg\min_\Theta \|Y - Y^*\|^2 \quad (1)$$

where Y can represent the machine parameters or fault detection or classification determined by the deep learning model, where $Y^*$ can represent the known machine parameters or the ground truth fault identification, and where $\Theta^*$ can represent model parameters of the deep learning model (e.g., layer node weights and biases as described above) corresponding to a minimized square error between Y and $Y^*$.

After updating the parameters of the deep learning model, the iteration index can be incremented by one. The iteration index can correspond to a number of times that the parameters of the deep learning model have been updated. Convergence or training stopping criteria can be checked at 734. In an embodiment, the convergence or stopping criteria can include a value of the iteration index (e.g., the convergence or stopping criteria can include whether the iteration index is greater than or equal to a determined maximum number of iterations), In an embodiment, the convergence or stopping criteria can include an accuracy of the output. set of machine parameters or accumulated estimation error (e.g., the convergence or stopping criteria can include whether the cumulative difference between the estimated DLG faults and the ground truth of the identified. DLG faults, across the batch of training data, is smaller than a threshold). In an example, the threshold can correspond to an asymptotic minimum of all errors determined.

If at 734 it is determined that the convergence or stopping criteria have been satisfied, then the trained DL model 740 can be saved in a memory, such as the memory device 116 of data processing device 112, and the training can be halted. The trained model 740 can he used during a testing or inference stage 712 to predict and diagnose DLG fault and generate the predicted results 744, using test DLG data. 742 collected from a. target radiotherapy system, The deep learning model, such as the CNN model or the RNN model (e.g., LSTM model) as discussed above, can involve many model parameters including, for example, sliding window length, the number of network layers, the number of hidden neurons, and the dropout. discarding rate, among others. To improve fault diagnosis, a grid search method can he used to optimize one or more model parameters. Grid search, also referred to as parameter sweep, is a process of scanning through a manually specified subset of the hyperparameter space of a learning algorithm, and build a model on each parameter combination. It iterates through every parameter combination and stores a. model for each combination, evaluate a performance metric for each parameter combination, and determine optimal parameter combination for a given model.

Compared to other hyperparametric optimization methods (e.g., genetic algorithm, random search algorithm, particle swarm optimization, Bayesian algorithm, etc.), grid search method is simple to implement and configured for parallel computing, and can meet the needs sequential DLG databased fault detection and classification.

In some examples, the deep learning model may be trained using a two-step approach. In a first step, a fault detection model is trained to detect an absence or a presence of a fault. In a subsequent second step, a fault diagnosis model is trained to classify each of the detected fault from the first step into one of fault classes, Because the first step essentially groups all positive samples of different fault types together, the two-step approach can advantageously help to reduce the impact of sample size imbalance and improve FDD accuracy.

Figure 9:
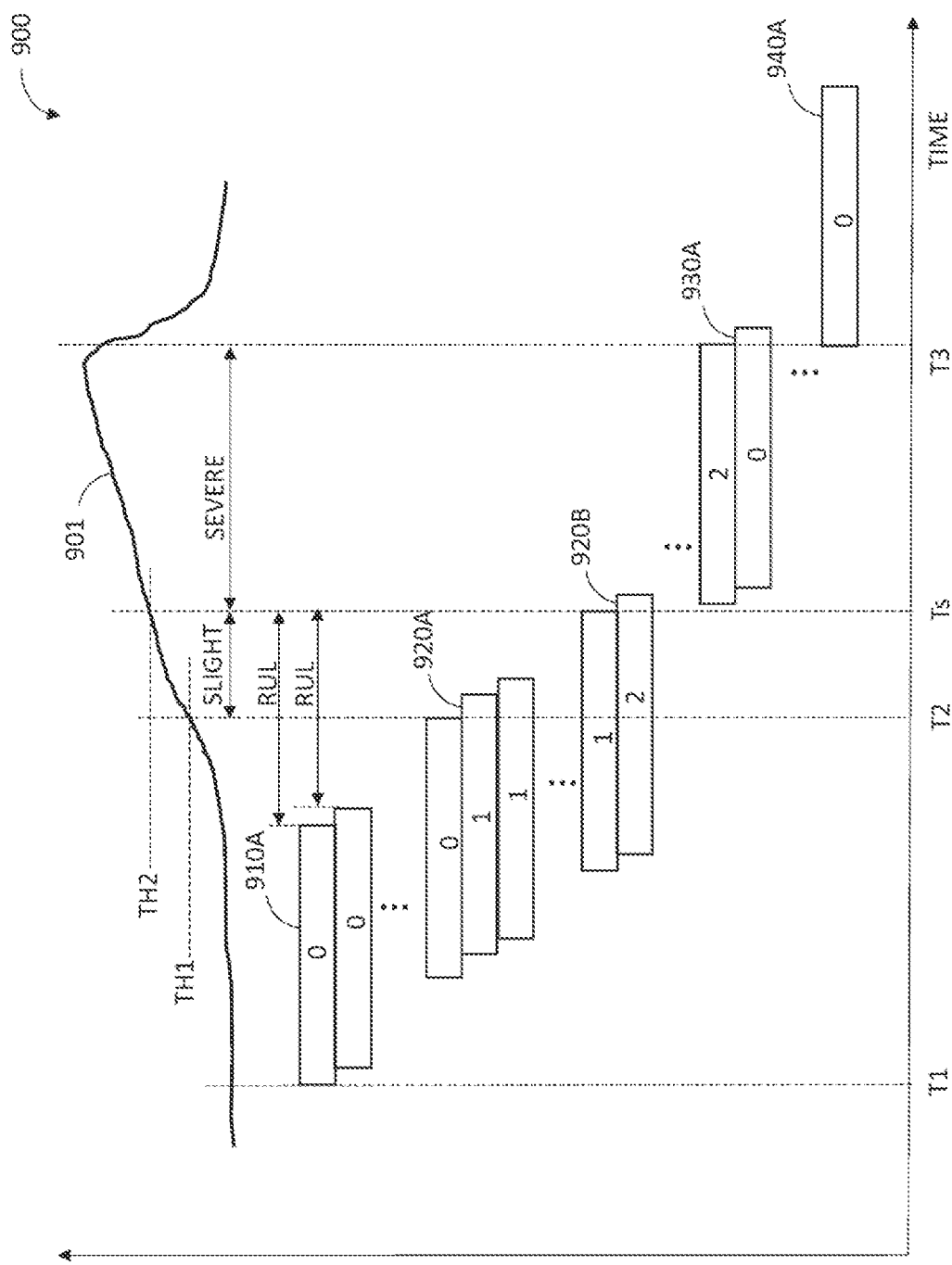
FIG. 9 is a diagram illustrating an example of generating training data to train an FDD deep learning model for fault detection and diagnosis.

In some examples, the trained model 740 can be evaluated before it is used to predict and diagnose faults using the test DLG data 742, The trained model 740 may be applied to a validation set, which may include, a set of DLG data samples such as data sequences as shown in FIG. 9 below. The validation data can be different from the training data 720. Each sample in the validation set may be recognized by the model 740 as one of a true positive (TP), false positive (FP), true negative (TN), and false negative (FN). TP represents a DLG data sample where the true value is positive (e.g., DLG being faulty or having a particular fault type Fx), and the DL model predicts the same fault status or fault type Fx. FN represents a DLG data sample where the true value is positive, and the DL model predicts the opposite (e.g., DLG is indeed faulty but model predicts no fault, or DLG has a particular fault type Fx but the model predicts a different fault type Fy). FP represents a DLG data sample where the true value is negative, but the model predicts the opposite (e.g., DLG being normal but the model predicts fault, or DLG does not have fault Fx but the model predicts Fx). TN represents a DLG data sample where the true value is negative (DLG being normal, or does not have fault Fx), and the DL model predicts the same.

Using the counts of TP, FN, FP, and TN samples recognized from the validation set, one or more performance metrics may be generated. In an example, the performance metric may include a precision (also referred to as positive predictive value), defined as TP/(PT+FP). The precision represents a fraction (e.g,, percentage) of all model-detected faulty DLGs of all types that are actually faulty, or the fraction of all model-detected faulty DLGs of a particular type that actually have said particular fault type. Another example of the performance metric may include a recall (also referred to as sensitivity), defined as TP/(TP+FN). The recall represents a fraction of all faulty DLGs of all types that are recognized by the model as faulty, or the fraction of all faulty DLGs of a particular type that are recognized by the model as having said particular fault type. Additionally or alternatively, the performance metric may include a balanced F1 score, defined as the harmonic mean of accuracy and recall, as given in the following formula. F1 score ranges between 0 and 1, where F1 reaches its best value at 1 (perfect precision and recall) and worst at 0.

$$F1 - \text{Score} = \frac{2}{\frac{1}{\text{precision}} + \frac{1}{\text{recall}}} = 2 \times \frac{\text{precision} \times \text{recall}}{\text{precision} + \text{recall}} \quad (2)$$

Another performance metric is Matthews Correlation Coefficient (MCC), as defined below. MCC is a correlation coefficient between the observed and predicted binary classifications, and takes a value between −1 and 1. The closer the value is to 1, the more accurate the model predicts.

$$MCC = \frac{TP \times TN - FP \times FN}{\sqrt{(TP + FP)(TP + FN)(TN + FP)(TN + FN)}} \quad (3)$$

In various examples, one or more performance metrics may be compared to a pre-set performance criterion, such as a performance threshold. If the performance metrics, determined based on the validation set, satisfy the performance criterion, then the rained DL model 740 can he used to predict and diagnose faults using the test DLG data 742; otherwise, one or more parameters of the model 740 can be adjusted, or the model 740 can be retrained using additional training DLG data.

In some examples, MCC can be used to modify the cost function used for training the DL model, such as the cost function given in Equation (1) above. Adding penalties for positive and negative sample imbalance in a cost function can not only improve the accuracy of training model, but also reduce the impact of data imbalance. The penalty term based on MCC (scaled by penalty weight λ) is introduced into the cost function to determine a loss. Equation (4) is an example of a loss function including a base loss component based on binary cross-entropy, and an additive penalty term based on MCC:

$$\text{Loss} = \text{binary\_crossentropy} + \lambda * (1 - \text{mcc}) \quad (4)$$

In some examples, the DL model may be trained using the process 700A to classify a DLG fault into one of a plurality of fault severity levels. The fault severity can be based on a trend of a DLG metric. For example, a fault is identified as a "severe" fault if the DLG metric value exceeds a specific threshold, or as a "slight" fault if the DLG metric value is below said specific threshold. To train a deep learning model such as according to the process 700A, a training dataset can be constructed such that each training sample (e.g., a DLG data sequence as shown in FIG. 9 below) is assigned with a severity level. The severity levels, which can be a part of the expected results 724, can take categorical or numerical values. The trained model 740 can be used to classify a fault detected from test DLG data 742 as a slight fault, or a severe fault. Examples of constructing the training dataset 720 and assigning respective severity levels to the training samples, are discussed with reference to FIG. 9.

In some examples, fault diagnosis may include a predicted time to fault, also referred to as remaining useful life (RUL). The RUL represents a time interval from the moment of a fault of a machine part being predicted to the time when said fault actually emerges and requires maintenance or replacement. Information about RUL can help maintenance personnel schedule maintenance, optimize operational efficiency, and avoid unplanned downtime. During model training such as according to the process 700A, a training dataset can be constructed such that a. RUL value can be determined for each training sample (e.g., a DLG data sequence as shown in FIG. 9 below). In an example, the RUL value can be represented by the number of days between the time of the training sample and the time when the DLG metric value reaches a specified threshold. The RUL values, which can be a part of the expected results 724, can be used to train the deep learning model to predict RUL for the test DLG 742. Examples of constructing the training dataset 720 and determining respective RUL values for the training samples are discussed with reference to FIG. 9.

Although the present document focuses on deep-learning based DLG fault detection and diagnosis, this is by way of example and not limitation. The systems, devices, processes according to various examples discussed in this document can be used to detect and diagnose fault associated with other parts or components (e.g., an MLC) of a radiotherapy system, as would be appreciated by those skilled in the art.

Figure 8:
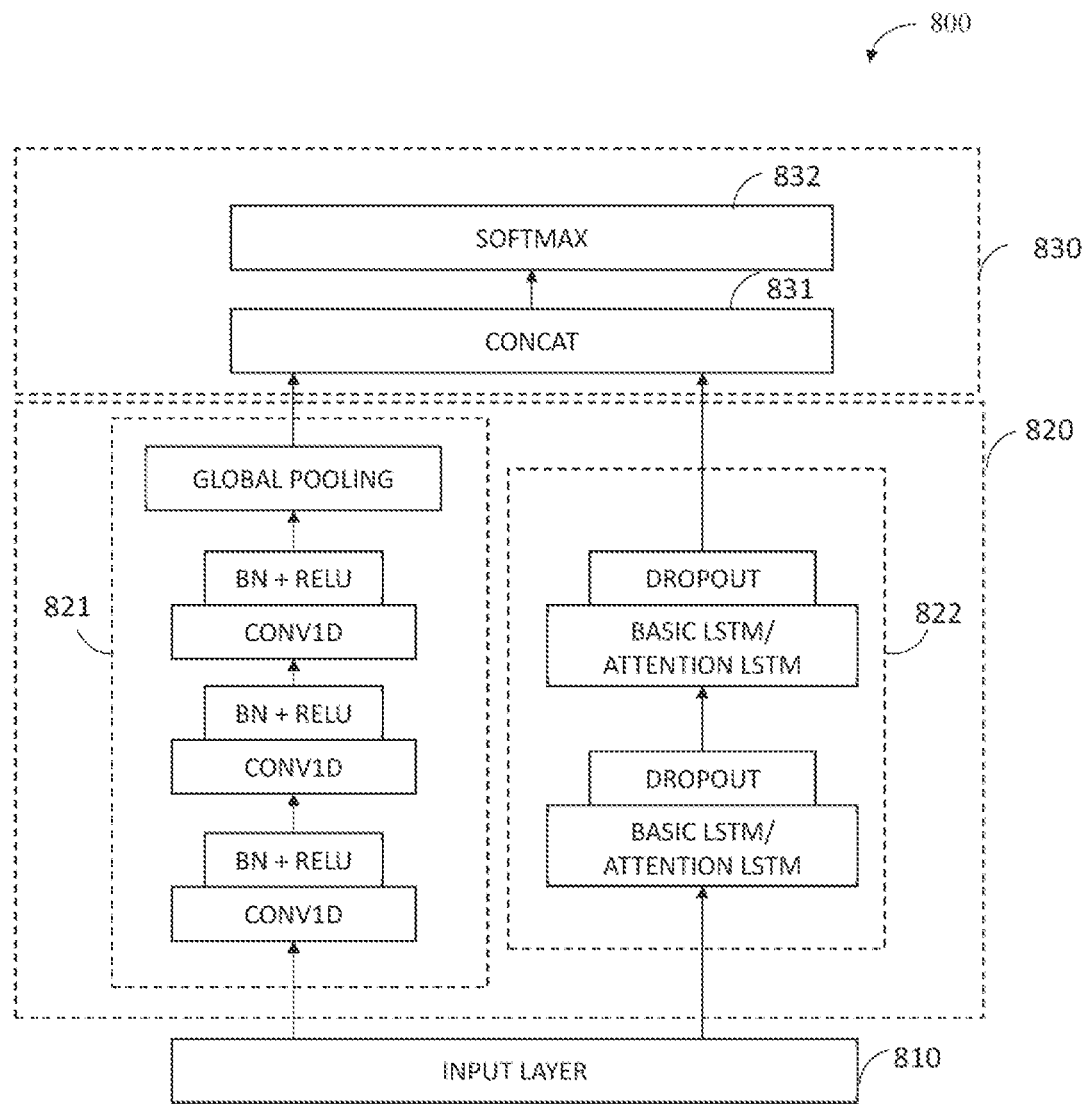
FIG. 8 is a diagram illustrating an exemplary architecture of an FDD deep learning model that combines two models, also referred to as model fusion.

FIG. 8 is a diagram illustrating an exemplary architecture of an FDD deep learning model 800 that combines two deep learning models, also referred to as model fusion (of sub-models). in an example, the sub-models being fused can be the same type of model having at least one different model parameter (e.g,, two CNN models with different model structures). In another example, the sub-models being fused can be different types of models (e.g., a CNN combined with an LSTM model). Because different deep learning models have different expressive ability after training, the integrated model can combine the strengths of the sub-models, and therefore improve the overall fault prediction and diagnose performance.

The example as illustrated in FIG. 8 includes a multi-layer deep learning model, including an input layer 810, a learning layer 820, and an output layer 830. The learning layer 820 comprises two different DL model, or DL models of the same type but different parameters. By way of example, the model fusion, denoted by "first model+second model", can include LSTM+LSTM, LSTM+CNN, or CNN+CNN, In the illustrated example, the first model 821 comprises three CNN layers (e.g,, three one-dimensional convolutional layer, or "CONV1D" layers). Each CNN layer includes a rectified linear unit (ReLU) activation function and a batch normalization (BN). The ReLU activation can help improving feature representation of the CNN model. The BU operation can alleviate the internal emanate. shift problem. The CONV-BN-ReLU sequence can improve the performance of the CNN network. The second model 822 includes two LSTM layers, with a dropout layer in between each to prevent the LSTM layer from overfitting. It is noted that the fusion of two models shown in FIG. 8 is for illustration but not limitation. In some examples, three or more models of the same or different types can be included in a fusion model, which has been contemplated by the present inventors and are within the scope of the present document.

The output layer 830 can include a concatenation layer 831 and a softmax activation layer 832. The concatenation layer 831 is a utility layer that concatenates multiple outputs from the first model 821 and the second model 822 into a single output. The softmax activation layer 832 applies a softmax function to the concatenated output to produce a categorical output representing presence or absence of a DLG fault, or a DLG fault type. In an example, the categorical output can be represented by integers, such as "0" for no fault, "1" for DLG brake fault, "2" for DLG circuit board fault, "3" for a hybrid fault involving both the brake and the circuit board, "4" for a drive motor fault, "5" for a DLG linear slide fault (e.g., greasing slide), or "6" for DLG coupling fault, among others.

FIG. 9 is a diagram illustrating an example of generating training data to train an FDD deep learning model that can detect and diagnose a fault associated with one or more components in a radiotherapy machine. The training 10 date can be constructed using measurements taken from a component, such as a DLG in a linac system. The measurements of a physical parameter (e.g., DLG current $I_{y1}$ or $I_{y2}$) or of a DLG metric can be trended over time to form a data sequence 901 (e.g., a time series). The data sequence 901 can be generated by trending a physical parameter or a DLG metric over time, such as the time series shown in FIGS. 6/. --6C. moving window 910, having a window size (L) of a specified number of days (e.g., 20-30 days), may slide along the time axis at a specified step size AL (e.g., 1 day). The DLG data within each data window form a training sample. The "expected results" for the training samples, such as fault labels representing fault presence/absence, fault type, or fault severity, can be determined based on temporal locations of the data windows relative to one or more reference times T1, T2, Ts, or T3. T1 represents the time of initiating the DLG fault prediction, where a window 910 begins to form a data sequence. T2 represents the time when the data sequence 901 crosses and exceeds a first threshold TH1, indicating an onset of an identified DLG fault (e.g, recognized by a human expert). Ts represents the time when the data sequence 901 crosses and exceeds a second threshold TH2. T3 represents the time when the identified DLG fault is corrected or resolved. The first and second thresholds, TH1 and TH2, can be determined by maintenance personnel based on engineering experience. In an example as illustrated in FIG. 9, TH2 can be greater than TH1. These thresholds are set to prevent early warning or late warning, and can be adjusted dynamically according to the performance of fault prediction and diagnosis.

When a window (e.g., window 910) falls completely prior to time T2 (i.e., the right edge of the window does not reach or pass T2), the training sample of said window is assigned with a fault label "0" to indicate an absence of DLG fault. When the moving window slides and begins to cross time T2 (e.g., window 920), the training sample of said window is assigned with a non-zero fault label (e.g., "1") to indicate a presence of a DLG fault. When the moving window slides and begins to cross time T3 (e.g., window 930), the training sample of said window is assigned with a label "0" to indicate the DLG fault has been corrected. The window sliding process then continues, until the left edge the window reaches time T3 (e.g., window 940). At this point in time, window sliding process stops. The data sequences thus generated (including, the window 910 to the window 940 and the intermediate windows), along with the fault labels associated with the training samples, form a training dataset. The training dataset may be used to train a deep learning model to detect and diagnose l LG fault, as discussed above with reference to FIG. 7A.

Distinct fault labels can be assigned to respective training samples to distinguish between different fault types, or between different fault severity. In an example, fault severity can be based on signal amplitude of the data sequence 901. As discussed above, reference time Ts is the time when the data sequence 901 crosses and exceeds a second threshold TH2. A data window can be labeled as a slight fault or a severe fault based on the temporal location of the data window relative to Ts. As illustrated in FIG. 9, a slight fault zone can be defined as a time interval between T2 and Ts, and a severe fault zone can be defined as a time interval between Ts and T3. A data window having its right edge falling between T2 and Ts (e.g., window 920A) is assigned with a label of slight fault (e.g., a numerical fault label "1"). Data sample within a slight fault window is below the threshold TH2. A data window having its right edge falling between Ts and T3 (e.g., window 920B) is assigned with a label of severe fault (e.g., a numerical fault label "2"). At least a portion of the data sample within a severe fault window exceeds the threshold TH2. The training samples in the data windows and their associated fault labels can be used to train the deep learning model to distinguish a slight fault from a severe fault.

FIG. 9 also illustrates determining time to fault, or remaining useful life (RUL), for the training samples in the data windows. For a data window, the RUL can be determined as an interval between the right edge of the data window and the reference time Ts. As such, RUL can be determined for each of the data windows having a fault labels "0" (no fault) and "1" (slight fault). The training samples in the data windows and their associated RUL values, can be used to train the deep learning model to predict a RUL for a given DLG.

In some examples, those data windows having a RUL less than a RUL threshold ($RUL_{TH}$) can be assigned with a different fault label (e.g., "11") to distinguish from the data windows having a RUL greater than $RUL_{TH}$, which can be assigned a different fault label (e.g., "12"). In an example, $RUL_{TH}$ is approximately 10 days. Compared to faults labeled as "12", faults labeled as "11" have a short RUL, thus may pose a higher risk of future failure and require elevated awareness and preventive maintenance by an service personnel. The training samples in the data windows and their associated fault labels (e.g., "11" and "12") can be used to train the deep learning model to distinguish between slight faults with different RULs.

Figure 10:
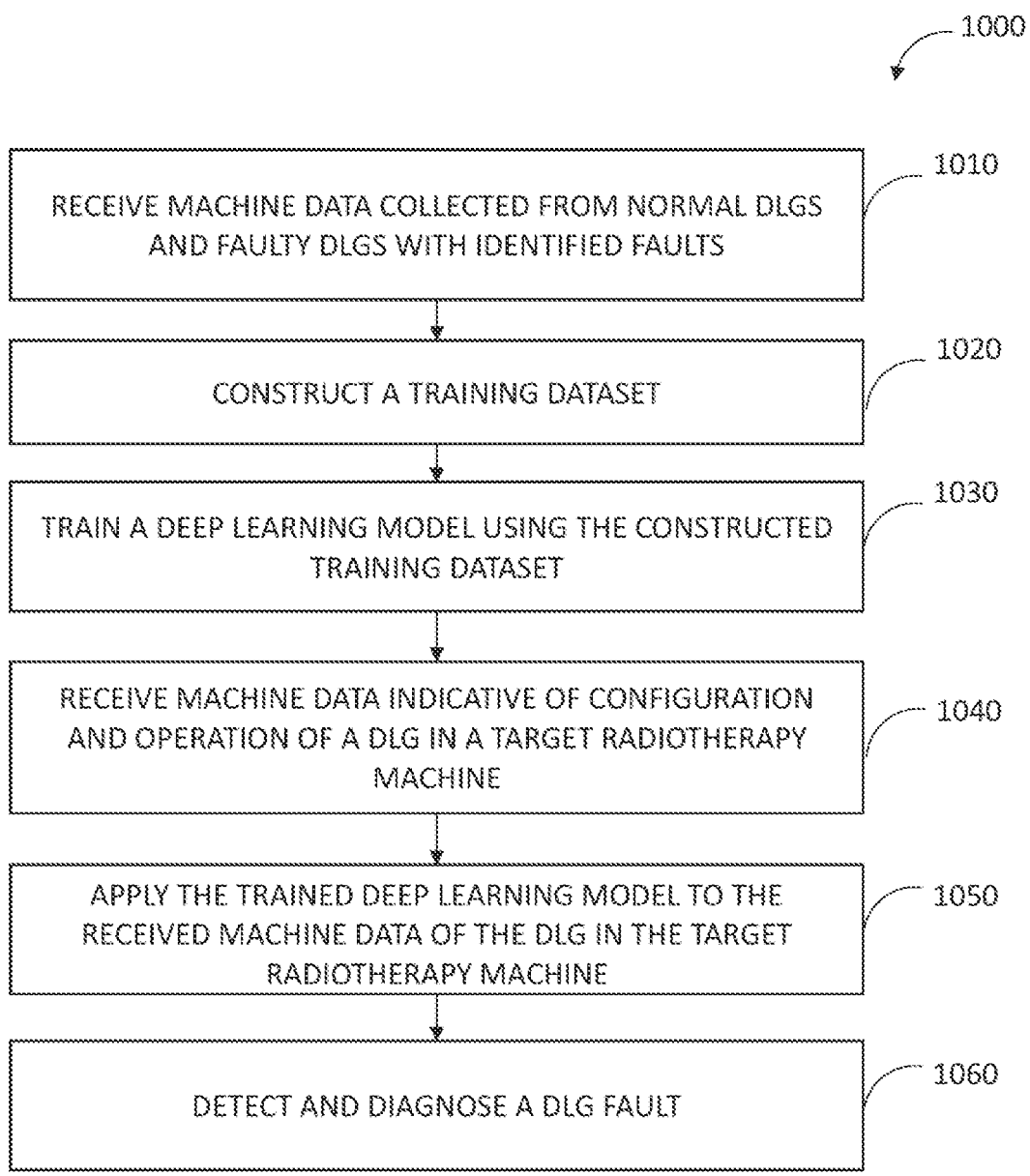
FIG. 10 is a flow chart illustrating an exemplary method of training and using a deep learning model to detect and diagnose a fault associated with a DLG in a radiotherapy system.

FIG. 10 is a flow-chart illustrating an exemplary method 1000 of detecting and diagnosing a fault in a radiotherapy machine configured to provide radiation therapy to a subject, such as a fault associated with a dynamic leaf guide (DLG) in a radiotherapy system, such as the system 202 or the system 300. The method 1000 may be embodied in computer-readable instructions for execution by one or more processors such that the operations of the method 1000 may be performed in part or in whole by the functional components of the data processing device 112; accordingly, the method 1000 is described below by way of example with reference thereto. However, in other embodiments, at least some of the operations of the method 1000 may be deployed on various other hardware configurations. The method 1000 is therefore not intended to be limited to the data processing device 112 and can be implemented in whole, or in part, by any other component. Some or all of the operations of method 1000 can be in parallel, out of order, or entirely omitted.

At 1010, machine data collected from one or more normal DLGs and one or more faulty DLGs with identified faults can be received, such as by the data processing device 112. The received machine data can be indicative of configuration and operation of respective DLGs, thus also referred to as DLG data. In some examples, the DLG data can include one or more DLG metrics, such as one or more statistical or cumulative DLG current metrics, one or more of the statistical or cumulative DLG out-of-position event counts, or one or more of the statistical or cumulative DLG alarm counts, as discussed above with reference to FIGS. 6A-6C. Along with the DLG data received at 1010 are fault labels for normal DLGs and faulty DLGs, which may be provided by a human expert. In an example, normal DLGs have a fault label of "0", and the faulty DLGs each have a fault label representing a particular fault type, such as "1" for DLG brake fault, "2" for DLG circuit board fault, "3" for a hybrid fault involving both the brake and the circuit board, "4" for a drive motor fault, "5" for a DLG linear slide fault (e.g., greasing slide), or "6" for DLG coupling fault (e.g., loose coupling), among other fault types.

At 1020 a training dataset can be constructed using the received machine data from both the normal and faulty DLGs. In some examples, values of a DLG metric may be trended over a specified time period to form a metric sequence (e.g., a time series), and training samples can be extracted using a moving data window, such as according to a process as illustrated in FIG. 9. For each training sample, a fault label can be provided such as by an human expert via a user interface, and assigned to the training sample. The fault label can take a numerical or categorical value, and represents fault presence/absence,, fault type, or fault severity. In some examples, the fault labels can be determined based on temporal locations of the data windows relative to one or more reference times, as illustrated in FIG. 9. A training sample and the corresponding fault label form an input-output training pair.

The training dataset may be processed to mitigate certain deficiencies, such as data imbalance between normal (fault-free) DLGs datasets (also referred to as "negative" samples) and faulty DLG datasets (also referred to as "positive" samples). Various techniques can be used to process the training dataset, including oversampling, penalty weight adjustment for positive and negative samples, and model integration are used to preprocess the training data. In an example, different. penalty weights are assigned to the positive and negative samples based at least on the sample size. The penalty weights can be inversely proportional to the sample size. The data imbalance may additionally or alternatively be mitigated using a data enhancement process, or a Synthetic Minority Oversampling Technique (SMOTE) to synthesize additional minority samples. Additionally or alternatively, to overcome inconsistency of sample distribution across different datasets, transfer learning module can be added to the deep learning model.

At 1030, a deep learning model can be trained using the constructed training dataset, such as using a process as illustrated in FIG. 7A. The deep learning model being trained can include a convolutional neural network (CNN), a recurrent neural network (RNN), a deep belief network (DBN), or a hybrid neural network comprising two or more neural network models of different types or different model configurations. FIGS. 7B and 7C illustrated examples of a CNN model and a long short-term memory (LsTM) network (a type of RAN model).

During the model training, model parameter can he updated to minimize or reduce a cost function. The cost function can include an estimation error term (e.g., sum of squared error term), such as given in Equation (1). The cost function may additionally include a penalty term. In an example, the penalty term is an L2 norm equal to the square of the magnitude of feature weights in the neural network model, and is used to control the model complexity. In another example, the penalty term may be based on a Matthews Correlation Coefficient (MCC), such as given by Equation (4). A convergence or training stopping criteria can be checked during model training. If it is determined that the convergence or stopping criteria have been satisfied, then the training can be halted. The trained model can he saved in a memory. In some examples, the trained model can be evaluated, and one or more performance metrics may be generated, which may include, a precision, a recall, a balanced F1 score, or MCC, among others.

At 1040, machine data indicative of configuration and operation of a DLG in a target radiotherapy machine can be received. DLG metrics may be generated from the machine data. At 1050, the trained deep learning model can be applied to the DLG metrics data corresponding to the DLG of the target radiotherapy machine. Depending on the fault labels assigned to the training samples in the training dataset, the trained model can be used to detect (including early detect or predict) fault presence or absence, classify a fault into one of a number of fault types, or to predict a fault severity level.

At 1060, presence of absence of a DLG fault can be detected using the trained model. The model can output fault diagnosis if a DLG is detected. Additionally or alternatively, fault diagnosis can be performed, such as by classifying a fault as one or more of a DLG brake fault, a DLG drive circuit board fault, a DLG drive motor fault, a DLG slide fault, or a DLG coupling unit fault, among others. The fault detection and diagnosis results can be presented to a user. The user may view the fault diagnostics and take actions such as performing further test, or make necessary repairs or other preventive or corrective actions.

In some examples, for each training sample, a time to fault, or remaining useful life (RUL), can be determined for the training sample, such as discussed above with reference to FIG. 9. The deep learning model can be trained to predict a RUL for the DLG in the target radiotherapy machine.

Figure 11:
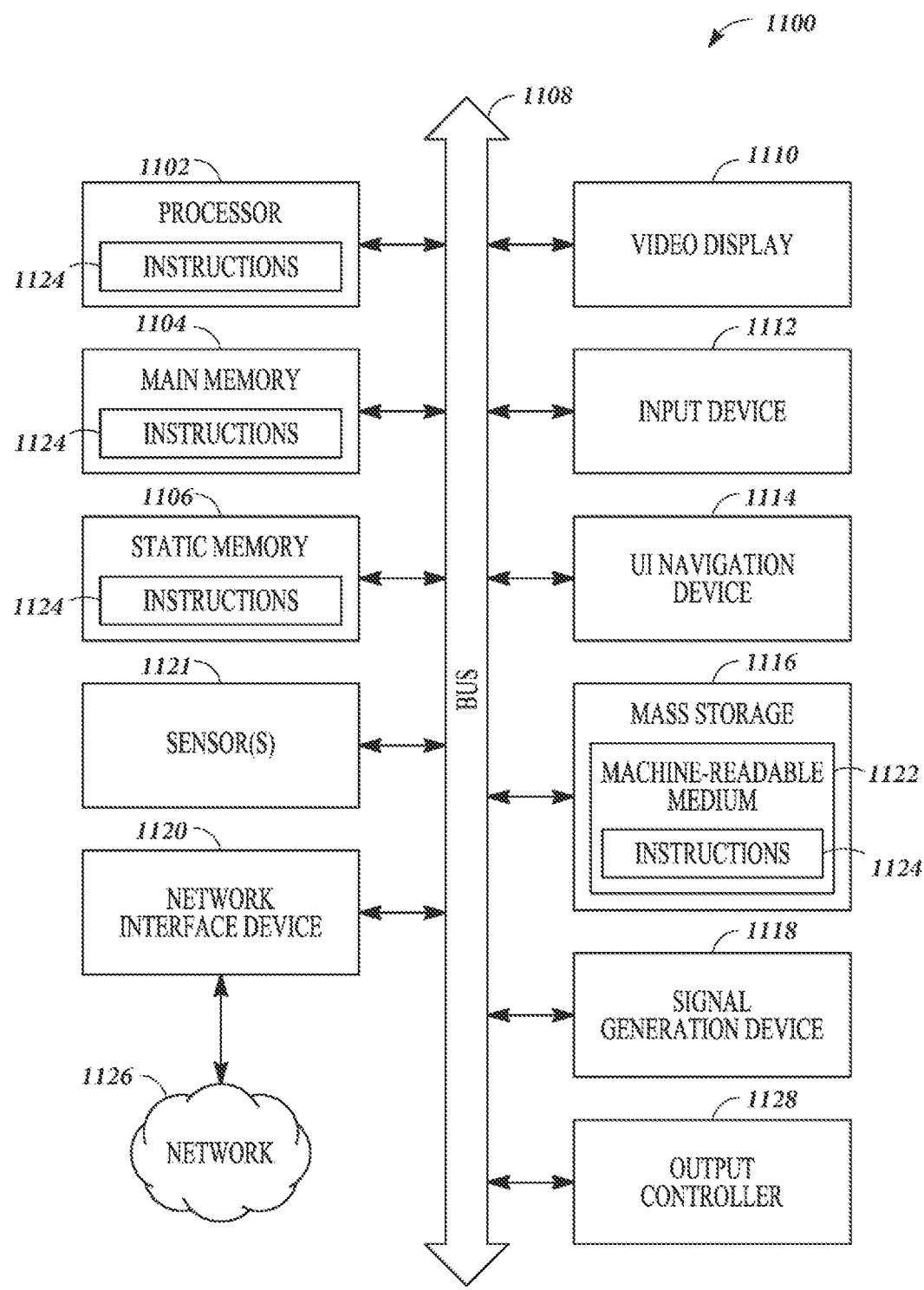
FIG. 11 illustrates an exemplary block diagram of a machine on which one or more of the methods as discussed herein can be implemented.

FIG. 11 illustrates a block diagram of an embodiment of a machine 1100 on which one or more of the methods as discussed herein can be implemented. In one or more embodiments, one or more items of the data processing device 112 can be implemented by the machine 1100. In alternative embodiments, the machine 1100 operates as a standalone device or may be connected (e.g., networked) to other machines. In one or MOM embodiments, the data processing device 112 can include one or more of the items of the machine 1100, In a networked deployment, the machine 1100 may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually, or jointly execute a set (or multiple sets) of instructions to perform any one or more of the methodologies discussed herein.

The example machine 1100 includes processing circuitry 1102 (e.g., a CPU, a. graphics processing unit (GPU), an ASIC,, circuitry, such as one or more transistors, resistors, capacitors, inductors, diodes, logic gates, multiplexers, buffers, modulators, demodulators, radios (e.g., transmit or receive radios or transceivers), sensors 1121 (e.g., a transducer that converts one form of energy (e.g., light, heat, electrical, mechanical, or other energy) to another form of energy), or the like, or a combination thereof), a main memory 1104 and a static memory 1106, which communicate with each other via a bus 1108. The machine 1100 (e.g., computer system may further include a video display unit 1110 (e.g., a liquid crystal display (LCD) or a cathode ray tube (CRT)). The machine 1100 also includes an alphanumeric input device 1112 (e.g., a keyboard), a user interface (UI) navigation device 1114 (e.g., a mouse), a disk drive or mass storage unit 1116, a signal generation device 1118 (e.g., a speaker), and a network interface device 1120.

The disk drive unit 1116 includes a machine-readable medium 1122 on which is stored one or more sets of instructions and data structures (e.g., software) 1124 embodying or utilized by any one or more of the methodologies or functions described herein. The instructions 1124 may also reside, completely or at least partially, within the main memory 1104 and/or within the processor 1102 during execution thereof by the machine 1100, the main memory 1104 and the processor 1102 also constituting machine-readable media.

The machine 1100 as illustrated includes an output controller 1128. The output controller 1128 manages data flow to/from the machine 1100. The output controller 1128 is sometimes called a device controller, with software that directly interacts with the output controller 1128 being called a device driver.

While the machine-readable medium 1122 is shown in an embodiment to be a single medium, the term "machine-readable medium" may include a single medium or multiple media a centralized or distributed database, and/or associated caches and servers) that store the one or more instructions or data. structures. The term "machine-readable medium" shall also be taken to include any tangible medium that is capable of storing, encoding or carrying instructions for execution by the machine and that cause the machine to perform any one or more of the methodologies of the present disclosure, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), EEPROM, and flash memory devices; magnetic disks such yrs internal hard disks and removable disks; magneto-optical disks; and CD-ROM and DVD-ROM disks.

The instructions 1124 may further be transmitted or received over a. communications network 1126 using a transmission medium. The instructions 1124 may be transmitted using the network interface device 1120 and any one of a number of well-known transfer protocols (e.g., HTTP). Examples of communication networks include a LAN, a WAN, the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

As used herein "communicatively coupled between" means that the entities on either of the coupling must communicate through an item therebetween and that those entities cannot communicate with each other without. communicating through the item.

Additional Notes

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended aspects, the terms "including" and "in which" are used as the plain-English equivalents of the respective terms "comprising" and "wherein." Also, in the following aspects, the terms "comprising," "including," and "having" are intended to be open-ended to mean that there may be additional elements other than the listed elements, such that after such a term (e.g., comprising, including, having) in a aspect are still deemed to fall within the scope of that aspect. Moreover, in the following aspects, the terms "first," "second," and "third," and so forth, are used merely as labels, and are not intended to impose numerical requirements on their objects.

Embodiments of the disclosure may be implemented with computer-executable instructions. The computer-executable instructions (e.g., software code) may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other embodiments of the disclosure may include different computer-executable instructions or components having more or less functionality than illustrated and described herein.

Method examples (e.g., operations and functions) described herein can be machine or computer-implemented at least in part (e.g., implemented as software code or instructions). Some examples can include a computer-readable medium or machine-readable medium encoded with instructions operable to configure an electronic device to perform methods as described in the above examples. An implementation of such methods can include software code, such as microcode, assembly language code, a higher-level language code, or the like (e.g., "source code"). Such software code can include computer readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CD-ROMS, magnetic-optical disks, removable optical disks (e.g., compact disks and digital video disks), flash memory devices, magnetic cassettes, memory cards or sticks (e.g., secure digital cards), RAMs (e.g., CMOS RAM and the like), recordable/non-recordable media (e.g., read only memories (ROMs)), EPROMS, EEPROMS, or any type of media suitable for storing electronic instructions, and the like. Such computer readable storage medium coupled to a computer system bus to be accessible by the processor and other parts of the OIS.

In an embodiment, the computer-readable storage medium may have encoded a data structure for a treatment planning, wherein the treatment plan may be adaptive. The data structure for the computer-readable storage medium may be at least one of a Digital Imaging and Communications in Medicine (DICOM) format, an extended DICOM format, a XML format, and the like. DICOM is an international communications standard that defines the format used to transfer medical image-related data between various types of medical equipment. DICOM RT refers to the communication standards that are specific to radiation therapy.

In various embodiments of the disclosure, the method of creating a component or module can be implemented in software, hardware, or a combination thereof. The methods provided by various embodiments of the present disclosure, for example, can be implemented in software by using standard programming languages such as, for example, C, C++, Java, Python, and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general purpose computer selectively activated or reconfigured by a computer program stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, several objects of the disclosure can be achieved and other advantageous results attained. Having described aspects of the disclosure in detail, it will be apparent that modifications and variations are possible without departing from the scope of aspects of the disclosure as defined in the appended aspects. As various changes could be made in the above constructions, products, and methods without departing from the scope of aspects of the disclosure, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments are apparent to those of skill in the art upon reviewing the above description. The scope of the disclosure should, therefore, be determined with reference to the appended aspects, along with the full scope of equivalents to which such aspects are entitled.

Also, in the above Detailed Description, various features may be grouped together to streamline the disclosure. This should not be interpreted as intending that an unexpected disclosed feature is essential to any aspect. Rather, inventive subject matter may lie in less than all features of a particular disclosed embodiment. Thus, the following aspects are hereby incorporated into the Detailed Description, with each aspect standing on its own as a separate embodiment. The scope of the disclosure should be determined with reference to the appended aspects, along with the full scope of equivalents to which such aspects are entitled. Further, the limitations of the following aspects are not written in means-plus-function format and are not intended to be interpreted based on 35 U.S.C. § 112, sixth paragraph, unless and until such aspect limitations expressly use the phrase "means for" followed by a statement of function void of further structure.

The Abstract is provided to comply with 37 C.F.R. § 1.72(b), to allow the reader to quickly ascertain the nature of the technical disclosure. It is submitted with the understanding that it will not be used to interpret or limit the scope or meaning of the aspects.

What is claimed is:

1. A computer-implemented method for detecting and diagnosing a fault in a radiotherapy machine, the method comprising:
   receiving machine data indicative of configuration and operation of a component of a particular type in a target radiotherapy machine;
   applying a trained deep learning model to the received machine data of the component in the target radiotherapy machine, the trained deep learning model being trained to establish a relationship between machine data collected from normal components and faulty components of the particular type in respective radiotherapy machines, and fault information, including fault presence or absence, and fault types, of the normal components and the faulty components;
   based on applying the trained deep learning model to the received machine data of the component in the target radiotherapy machine, detecting and diagnosing a fault associated with the component in the target radiotherapy machine, wherein diagnosing the fault includes, in response to a detection of fault presence, classifying the detected fault into one of a plurality of pre-determined distinct fault types associated with the component; and
   alerting a user of the detected and diagnosed fault and initiating predictive maintenance of the target radiotherapy machine in accordance with the detected and diagnosed fault.

2. The method of claim 1, further comprising:
   receiving the machine data collected from the normal components and the faulty components with respectively identified faults, the machine data indicative of configuration and operation of respective components;
   constructing a training dataset including a plurality of data sequences generated from the received machine data of the normal components and the faulty components; and
   training a deep learning model using the constructed training dataset to establish the trained deep learning model.

3. The method of claim 2, wherein the component in the target radiotherapy machine includes a dynamic leaf guide (DLG), the normal components include normal DLGs, and the faulty components include faulty DLGs with respectively identified DLG faults, and
   wherein detecting and diagnosing the fault includes detecting and diagnosing a DLG fault in the target radiotherapy machine.

4. The method of claim 3, wherein training the deep learning model includes:
   applying respective penalty weights to one or more of the plurality of data sequences in the training dataset; and
   training the deep learning model using the constructed training dataset including the weighted data sequences.

5. The method of claim 3, wherein the deep learning model being trained includes one or more of:
   a convolutional neural network (CNN);
   a recurrent neural network (RNN);
   a long-term and short-term memory (LSTM) network;
   a deep belief network (DBN); or
   a transfer learning module.

6. The method of claim 3, comprising generating the plurality of data sequences including a trend of DLG current measurements over time, the DLG current measured respectively from one or more DLGs at respective axes.

7. The method of claim 6, wherein the DLG current trend includes one or more of:
   a trend of daily average current;
   a trend of daily variation current;
   a trend of daily maximum current;
   a trend of multiday moving-average of current.

8. The method of claim 3, comprising generating the plurality of data sequences including a trend of a DLG position metric over time, the DLG position metric calculated respectively for one or more DLGs at respective axes.

9. The method of claim 8, wherein the DLG position metric includes a count of DLG out-of-position events occurred during a specific time period, and the DLG position trend includes one or more of:
   a trend of daily count of out-of-position events; or
   a trend of cumulative count of out-of-position events over a specified number of days.

10. The method of claim 3, comprising generating the plurality of data sequences including a trend of alarms triggered by one or more alarm events, the alarm trends including one or more of:
    a trend of daily count of alarms; or
    a trend of cumulative count of alarms over a specified number of days.

11. The method of claim 3, wherein constructing the training dataset includes assigning a fault type to each of the plurality of data sequences, and wherein diagnosing the DLG fault in the target radiotherapy machine includes classifying the DLG fault as one or more fault types including:

a DLG brake fault;
a DLG drive circuit board fault;
a DLG drive motor fault;
a DLG slide fault; or
a DLG coupling unit fault.

12. The method of claim 3, wherein constructing the training dataset includes assigning a respective fault severity level to each of the plurality of data sequences, and wherein diagnosing the DLG fault in the target radiotherapy machine includes classifying the DLG fault as one of a plurality of fault severity levels.

13. The method of claim 3, wherein training the deep learning model includes determining for each of the plurality of data sequences a corresponding remaining useful life (RUL), and establishing a relationship between the plurality of data sequences and the corresponding determined RULs; and the method comprising using the trained deep learning model to predict a RUL for the DLG in the target radiotherapy machine.

14. The method of claim 3, wherein training the deep learning model includes adjusting one or more model parameters to minimize a cost function, the cost function including a penalty term based on a Matthews Correlation Coefficient (MCC).

15. A system for detecting and diagnosing a fault in a radiotherapy machine configured to provide radiation therapy to a subject, the system comprising a processor configured to:
receive machine data indicative of configuration and operation of a component of a particular type in a target radiotherapy machine;
apply a trained deep learning model to the received machine data of the component in the target radiotherapy machine, the trained deep learning model being trained to establish a relationship between (1) machine data collected from normal components and faulty components of the particular type in respective radiotherapy machines, and (2) fault information, including fault presence or absence, and fault types, of the normal components and the faulty components;
based on applying the trained deep learning model to the received machine data of the component in the target radiotherapy machine, detect and diagnose a fault associated with the component in the target radiotherapy machine, wherein to diagnose the fault includes, in response to a detection of fault presence, to classify the detected fault into one of a plurality of pre-determined distinct fault types associated with the component; and
alert a user of the detected and diagnosed fault and initiate predictive maintenance of the target radiotherapy machine in response to accordance with the detected and diagnosed fault.

16. The system of claim 15, wherein the processor includes a training module configured to:
receive the machine data collected from the normal components and the faulty components with respectively identified faults, the machine data indicative of configuration and operation of respective components;
construct a training dataset including a plurality of data sequences generated from the received machine data of the normal components and the faulty components; and
establish the trained deep learning model by training a deep learning model using the constructed training dataset.

17. The system of claim 16, wherein the component in the target radiotherapy machine includes a dynamic leaf guide (DLG), the normal components include normal DLGs, and the faulty components include faulty DLGs with respectively identified DLG faults, and wherein the processor is configured to detect and diagnose a DLG fault in the target radiotherapy machine.

18. The system of claim 17, wherein the processor is configured to construct the training dataset using fault information of each of the plurality of data sequences, the fault information including an indicator of fault presence or absence, fault type, or fault severity level.

19. The system of claim 17, wherein the training module is configured to generate the plurality of data sequences including one or more of:
a trend of DLG current measurements over time;
a trend of a DLG position metric over time, the DLG position metric including a count of DLG out-of-position events occurred during a specific time period; or
a trend of a count of alarms triggered by one or more alarm events.

20. A non-transitory machine-readable storage medium that includes instructions that, when executed by one or more processors of a machine, cause the machine to perform operations comprising:
receiving machine data indicative of configuration and operation of a component of a particular type in a target radiotherapy machine;
applying a trained deep learning model to the received machine data of the component in the target radiotherapy machine, the trained deep learning model being trained to establish a relationship between machine data collected from normal components and faulty components of the particular type in respective radiotherapy machines, and fault information, including fault presence or absence, and fault types, of the normal components and the faulty components;
based on applying the trained deep learning model to the received machine data of the component in the target radiotherapy machine, detecting and diagnosing a fault associated with the component in the target radiotherapy machine, wherein diagnosing the fault includes, in response to a detection of fault presence, classifying the detected fault into one of a plurality of pre-determined distinct fault types associated with the component; and alerting a user of the detected and diagnosed fault and initiating predictive maintenance of the target radiotherapy machine in accordance with the detected and diagnosed fault.

21. The non-transitory machine-readable storage medium of claim 20, wherein the operations further comprise:
receiving the machine data collected from the normal components and the faulty components with identified faults, the machine data indicative of configuration and operation of respective components;
constructing a training dataset including a plurality of data sequences generated from the received machine data of the normal components and the faulty components; and
training a deep learning model using the constructed training dataset to establish the trained deep learning model.

22. The non-transitory machine-readable storage medium of claim 21, wherein the component in the target radiotherapy machine includes a dynamic leaf guide (DLG), the normal components include normal DLGs, and the faulty components include faulty DLGs with respectively identified DLG faults, and wherein the operation of detecting and diagnosing the fault includes detecting and diagnosing a DLG fault in the target radiotherapy machine.

23. The non-transitory machine-readable storage medium of claim 22, wherein the operations further comprise diagnosing the DLG fault in the target radiotherapy machine includes classifying the DLG fault as one or more of:

a DLG brake fault;
a DLG drive circuit board fault;
a DLG drive motor fault;
a DLG slide fault; or
a DLG coupling unit fault.

* * * * *